(12) United States Patent
Villarta

(10) Patent No.: US 11,167,128 B2
(45) Date of Patent: Nov. 9, 2021

(54) DIRECTIONAL ELECTRICAL STIMULATION LEADS, SYSTEMS AND METHODS FOR SPINAL CORD STIMULATION

(71) Applicant: Boston Scientific Neuromodulation Corporation, Valencia, CA (US)

(72) Inventor: Geoffrey Abellana Villarta, Castaic, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 195 days.

(21) Appl. No.: 16/678,869

(22) Filed: Nov. 8, 2019

(65) Prior Publication Data

US 2020/0155833 A1 May 21, 2020

Related U.S. Application Data

(60) Provisional application No. 62/768,703, filed on Nov. 16, 2018.

(51) Int. Cl.
*A61N 1/05* (2006.01)

(52) U.S. Cl.
CPC .......... *A61N 1/0551* (2013.01); *A61N 1/0529* (2013.01)

(58) Field of Classification Search
CPC .......................... A61N 1/0551; A61N 1/0529
See application file for complete search history.

(56) References Cited

U.S. PATENT DOCUMENTS

| | | |
|---|---|---|
| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,070,605 A | 12/1991 | Daglow et al. |
| 5,135,001 A | 8/1992 | Sinofsky et al. |
| 5,348,841 A | 9/1994 | Ortiz |
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |

(Continued)

FOREIGN PATENT DOCUMENTS

| | | |
|---|---|---|
| EP | 0580928 A1 | 2/1994 |
| EP | 0650694 B1 | 7/1998 |

(Continued)

*Primary Examiner* — Mark W. Bockelman
(74) *Attorney, Agent, or Firm* — Branch Partners PLLC; Bruce E. Black

(57) ABSTRACT

An electrical stimulation lead includes terminals disposed along the proximal portion of the electrical stimulation lead; segmented electrodes disposed along the distal portion of the electrical stimulation lead; conductors electrically coupling the terminals to the electrodes; and an electrode carrier with divider segments extending from shoulder segments and disposed between, and separating, at least two of the segmented electrodes. The electrical stimulation lead can be formed by disposing electrode strips on an electrode carrier, each of the electrode strips comprising a plurality of pre-electrodes and at least one connection region in an alternating, longitudinal arrangement with one of the at least one connection region disposed between each adjacent pair of the pre-electrodes of the electrode strip; and removing each of the connection region(s) to separate the pre-electrodes into segmented electrodes.

13 Claims, 14 Drawing Sheets

(56) References Cited

U.S. PATENT DOCUMENTS

| | | | |
|---|---|---|---|
| 5,713,922 | A | 2/1998 | King |
| 5,800,350 | A | 9/1998 | Coppleson et al. |
| 5,843,148 | A | 12/1998 | Gijsbers et al. |
| 5,938,688 | A | 8/1999 | Schiff |
| 5,987,361 | A | 11/1999 | Mortimer |
| 6,018,684 | A | 1/2000 | Bartig et al. |
| 6,125,302 | A | 9/2000 | Kuzma |
| 6,134,478 | A | 10/2000 | Spehr |
| 6,161,047 | A | 12/2000 | King et al. |
| 6,162,101 | A | 12/2000 | Fischer et al. |
| 6,167,311 | A | 12/2000 | Rezai |
| 6,181,969 | B1 | 1/2001 | Gord |
| 6,295,944 | B1 | 10/2001 | Lovett |
| 6,305,962 | B1 | 10/2001 | Maher et al. |
| 6,322,559 | B1 | 11/2001 | Daulton et al. |
| 6,391,985 | B1 | 5/2002 | Goode et al. |
| 6,428,336 | B1 | 8/2002 | Akerfeldt |
| 6,510,347 | B2 | 1/2003 | Borkan |
| 6,516,227 | B1 | 2/2003 | Meadows et al. |
| 6,556,873 | B1 | 4/2003 | Smits |
| 6,564,078 | B1 | 5/2003 | Marino et al. |
| 6,609,029 | B1 | 8/2003 | Mann et al. |
| 6,609,032 | B1 | 8/2003 | Woods et al. |
| 6,663,570 | B2 | 12/2003 | Mott et al. |
| 6,678,564 | B2 | 1/2004 | Ketterl et al. |
| 6,741,892 | B1 | 5/2004 | Meadows et al. |
| 6,757,970 | B1 | 7/2004 | Kuzma et al. |
| 7,027,852 | B2 | 4/2006 | Helland |
| 7,047,084 | B2 | 5/2006 | Erickson et al. |
| 7,108,549 | B2 | 9/2006 | Lyu et al. |
| 7,203,548 | B2 | 4/2007 | Whitehurst et al. |
| 7,241,180 | B1 | 7/2007 | Rentas |
| 7,244,150 | B1 | 7/2007 | Brase et al. |
| 7,292,890 | B2 | 11/2007 | Whitehurst et al. |
| 7,402,083 | B2 | 7/2008 | Kast et al. |
| 7,437,193 | B2 | 10/2008 | Parramon et al. |
| 7,450,997 | B1 | 11/2008 | Pianca et al. |
| 7,489,971 | B1 | 2/2009 | Franz |
| 7,668,601 | B2 | 2/2010 | Hegland et al. |
| 7,672,734 | B2 | 3/2010 | Anderson et al. |
| 7,736,191 | B1 | 6/2010 | Sochor |
| 7,761,165 | B1 | 7/2010 | He et al. |
| 7,761,985 | B2 | 7/2010 | Hegland et al. |
| 7,783,359 | B2 | 8/2010 | Meadows |
| 7,792,590 | B1 | 9/2010 | Pianca et al. |
| 7,798,864 | B2 | 9/2010 | Barker et al. |
| 7,809,446 | B2 | 10/2010 | Meadows |
| 7,822,482 | B2 | 10/2010 | Gerber |
| 7,840,188 | B2 | 11/2010 | Kurokawa |
| 7,848,802 | B2 | 12/2010 | Goetz |
| 7,856,707 | B2 | 12/2010 | Cole |
| 7,860,570 | B2 | 12/2010 | Whitehurst et al. |
| 7,949,395 | B2 | 5/2011 | Kuzma |
| 7,974,705 | B2 | 7/2011 | Zdeblick et al. |
| 7,974,706 | B2 | 7/2011 | Moffitt et al. |
| 7,979,140 | B2 | 7/2011 | Schulman |
| 8,000,808 | B2 | 8/2011 | Hegland et al. |
| 8,019,440 | B2 | 9/2011 | Kokones et al. |
| 8,036,755 | B2 | 10/2011 | Franz |
| 8,041,309 | B2 | 10/2011 | Kurokawa |
| 8,046,074 | B2 | 10/2011 | Barker |
| 8,099,177 | B2 | 1/2012 | Dahlberg |
| 8,100,726 | B2 | 1/2012 | Harlan et al. |
| 8,140,163 | B1 | 3/2012 | Daglow et al. |
| 8,175,710 | B2 | 5/2012 | He |
| 8,190,259 | B1 | 5/2012 | Smith |
| 8,224,450 | B2 | 7/2012 | Brase |
| 8,225,504 | B2 | 7/2012 | Dye et al. |
| 8,239,042 | B2 | 8/2012 | Chinn et al. |
| 8,271,094 | B1 | 9/2012 | Moffitt et al. |
| 8,295,944 | B2 | 10/2012 | Howard et al. |
| 8,301,255 | B2 | 10/2012 | Barker |
| 8,321,025 | B2 | 11/2012 | Bedenbaugh |
| 8,342,887 | B2 | 1/2013 | Gleason et al. |
| 8,359,107 | B2 | 1/2013 | Pianca et al. |
| 8,364,278 | B2 | 1/2013 | Pianca et al. |
| 8,391,985 | B2 | 3/2013 | McDonald |
| 8,483,237 | B2 | 7/2013 | Zimmermann et al. |
| 8,583,237 | B2 | 11/2013 | Bedenbaugh |
| 8,688,235 | B1 | 4/2014 | Pianca et al. |
| 8,831,742 | B2 | 9/2014 | Pianca et al. |
| 8,849,415 | B2 | 9/2014 | Bedenbaugh |
| 8,968,331 | B1 | 3/2015 | Sochor |
| 9,101,775 | B2 | 8/2015 | Barker |
| 9,149,630 | B2 | 10/2015 | Howard et al. |
| 9,162,048 | B2 | 10/2015 | Romero et al. |
| 9,270,070 | B2 | 2/2016 | Pianca |
| 9,289,596 | B2 | 3/2016 | Leven |
| 9,352,147 | B2 | 5/2016 | Nguyen-stella |
| 9,381,348 | B2 | 7/2016 | Romero et al. |
| 9,403,022 | B2 | 8/2016 | Ries et al. |
| 9,409,032 | B2 | 8/2016 | Brase et al. |
| 9,440,066 | B2 | 9/2016 | Black |
| 9,498,620 | B2 | 11/2016 | Romero et al. |
| 9,504,839 | B2 | 11/2016 | Leven |
| 9,555,234 | B2 | 1/2017 | Duijsens et al. |
| 2001/0023368 | A1 | 9/2001 | Black et al. |
| 2002/0156513 | A1 | 10/2002 | Borkan |
| 2002/0183817 | A1 | 12/2002 | Van Venrooij et al. |
| 2005/0015130 | A1 | 1/2005 | Gill |
| 2005/0038489 | A1 | 2/2005 | Grill |
| 2005/0171587 | A1 | 8/2005 | Daglow et al. |
| 2006/0025841 | A1 | 2/2006 | McIntyre |
| 2006/0247697 | A1 | 11/2006 | Sharma et al. |
| 2007/0150036 | A1 | 6/2007 | Anderson |
| 2007/0168007 | A1 | 7/2007 | Kuzma et al. |
| 2007/0203546 | A1 | 8/2007 | Stone et al. |
| 2007/0219551 | A1 | 9/2007 | Honour et al. |
| 2008/0077186 | A1 | 3/2008 | Thompson et al. |
| 2008/0103580 | A1 | 5/2008 | Gerber |
| 2008/0114230 | A1 | 5/2008 | Addis |
| 2008/0215125 | A1 | 9/2008 | Farah et al. |
| 2008/0255647 | A1 | 10/2008 | Jensen et al. |
| 2009/0054941 | A1 | 2/2009 | Eggen et al. |
| 2009/0187222 | A1 | 7/2009 | Barker |
| 2009/0204192 | A1 | 8/2009 | Carlton et al. |
| 2009/0276021 | A1 | 11/2009 | Meadows et al. |
| 2010/0030298 | A1 | 2/2010 | Martens et al. |
| 2010/0036468 | A1 | 2/2010 | Decre et al. |
| 2010/0057176 | A1 | 3/2010 | Barker |
| 2010/0070009 | A1 | 3/2010 | Barker |
| 2010/0070012 | A1 | 3/2010 | Chinn et al. |
| 2010/0076535 | A1 | 3/2010 | Pianca et al. |
| 2010/0077606 | A1 | 4/2010 | Black et al. |
| 2010/0082076 | A1 | 4/2010 | Lee et al. |
| 2010/0094387 | A1 | 4/2010 | Pianca et al. |
| 2010/0100152 | A1 | 4/2010 | Martens et al. |
| 2010/0268298 | A1 | 10/2010 | Moffitt et al. |
| 2010/0269338 | A1 | 10/2010 | Dye |
| 2010/0269339 | A1 | 10/2010 | Dye et al. |
| 2010/0287770 | A1 | 11/2010 | Dadd et al. |
| 2011/0004267 | A1 | 1/2011 | Meadows |
| 2011/0005069 | A1 | 1/2011 | Pianca |
| 2011/0047795 | A1 | 3/2011 | Turner et al. |
| 2011/0056076 | A1 | 3/2011 | Hegland et al. |
| 2011/0077699 | A1 | 3/2011 | Swanson et al. |
| 2011/0078900 | A1 | 4/2011 | Pianca et al. |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0131808 | A1 | 6/2011 | Gill |
| 2011/0238129 | A1 | 9/2011 | Moffitt et al. |
| 2011/0245903 | A1 | 10/2011 | Schulte et al. |
| 2011/0301665 | A1 | 12/2011 | Mercanzini et al. |
| 2011/0313500 | A1 | 12/2011 | Barker et al. |
| 2012/0016378 | A1 | 1/2012 | Pianca et al. |
| 2012/0046710 | A1 | 2/2012 | DiGiore et al. |
| 2012/0071937 | A1 | 3/2012 | Sundaramurthy et al. |
| 2012/0071949 | A1 | 3/2012 | Pianca et al. |
| 2012/0165911 | A1 | 6/2012 | Pianca |
| 2012/0197375 | A1 | 8/2012 | Pianca et al. |
| 2012/0203302 | A1 | 8/2012 | Moffitt et al. |
| 2012/0203316 | A1 | 8/2012 | Moffitt et al. |

(56) References Cited

U.S. PATENT DOCUMENTS

| | | |
|---|---|---|
| 2012/0203320 A1 | 8/2012 | DiGiore et al. |
| 2012/0203321 A1 | 8/2012 | Moffitt et al. |
| 2012/0232603 A1 | 9/2012 | Sage |
| 2012/0259386 A1 | 10/2012 | DeRohan et al. |
| 2012/0316615 A1 | 12/2012 | DiGiore et al. |
| 2013/0105071 A1 | 5/2013 | DiGiore et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0197603 A1 | 8/2013 | Eiger |
| 2013/0261684 A1 | 10/2013 | Howard |
| 2013/0288501 A1 | 10/2013 | Russell et al. |
| 2013/0304140 A1 | 11/2013 | Derohan et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0180375 A1 | 6/2014 | Pianca et al. |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0021817 A1 | 1/2015 | Romero et al. |
| 2015/0045864 A1 | 2/2015 | Howard |
| 2015/0066120 A1 | 3/2015 | Govea |
| 2015/0127063 A1 | 5/2015 | Datta |
| 2015/0151113 A1 | 6/2015 | Govea et al. |
| 2015/0360023 A1 | 12/2015 | Howard et al. |
| 2015/0374978 A1 | 12/2015 | Howard et al. |
| 2016/0059019 A1 | 3/2016 | Malinowski et al. |
| 2016/0129242 A1 | 5/2016 | Malinowski |
| 2016/0129265 A1 | 5/2016 | Malinowski |
| 2016/0228692 A1 | 8/2016 | Steinke et al. |
| 2016/0296745 A1 | 10/2016 | Govea et al. |
| 2017/0014635 A1 | 1/2017 | Villarta et al. |
| 2017/0143978 A1 | 5/2017 | Barker |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 1997032628 A1 | 9/1997 |
| WO | 1999055411 A3 | 2/2000 |
| WO | 2000038574 A1 | 7/2000 |
| WO | 2001058520 A1 | 8/2001 |
| WO | 2002068042 A1 | 9/2002 |
| WO | 2004045707 A1 | 6/2004 |
| WO | 2008018067 A2 | 2/2008 |
| WO | 2008053789 A1 | 5/2008 |
| WO | 2008100841 | 8/2008 |
| WO | 2009025816 A1 | 2/2009 |
| WO | 2009102536 A1 | 8/2009 |
| WO | 2009/148939 | 12/2009 |
| WO | 2013162775 A2 | 10/2013 |
| WO | 2014018092 A1 | 1/2014 |

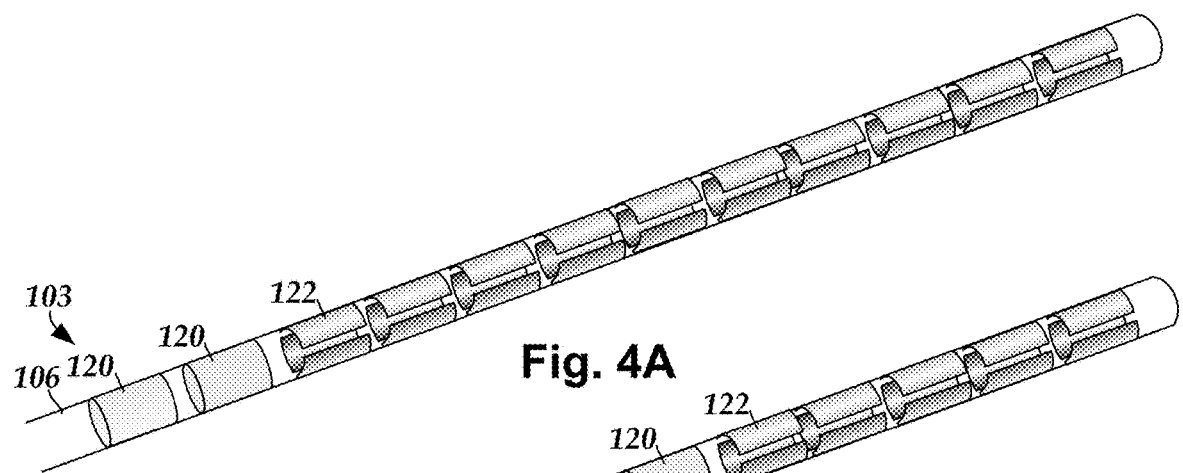
Fig. 4A
Fig. 4B
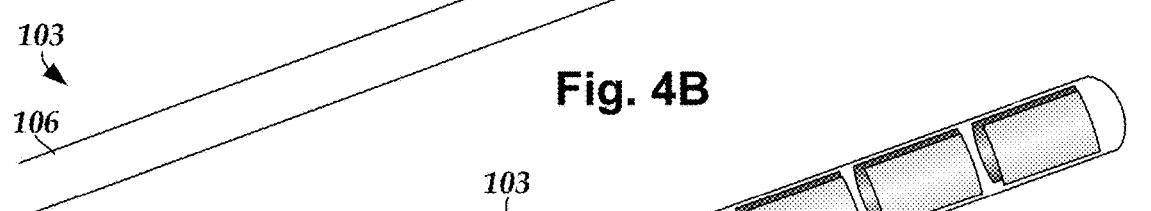
Fig. 4C
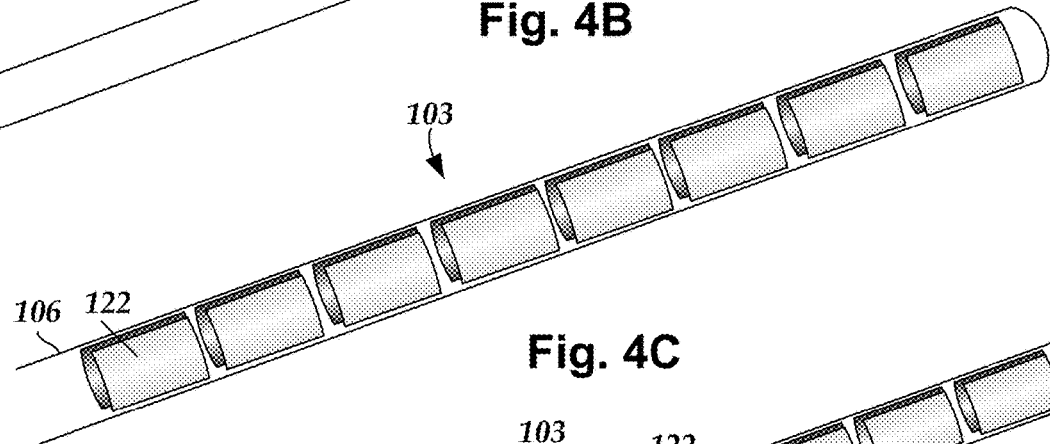
Fig. 4D
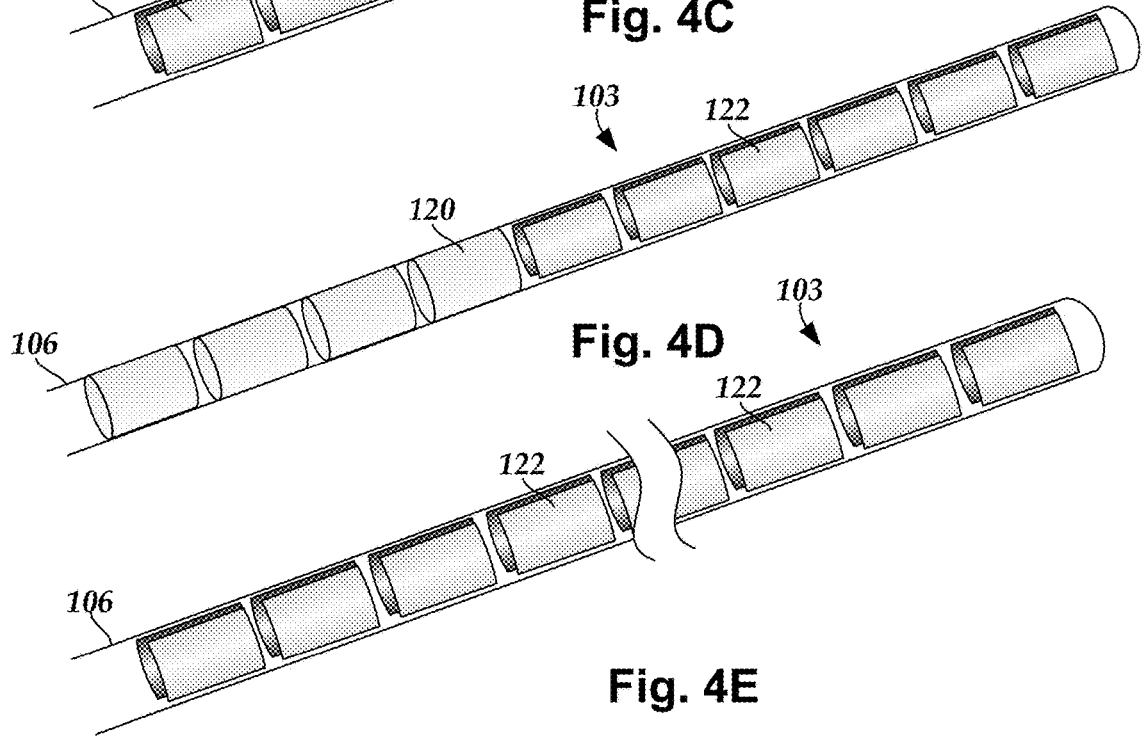
Fig. 4E

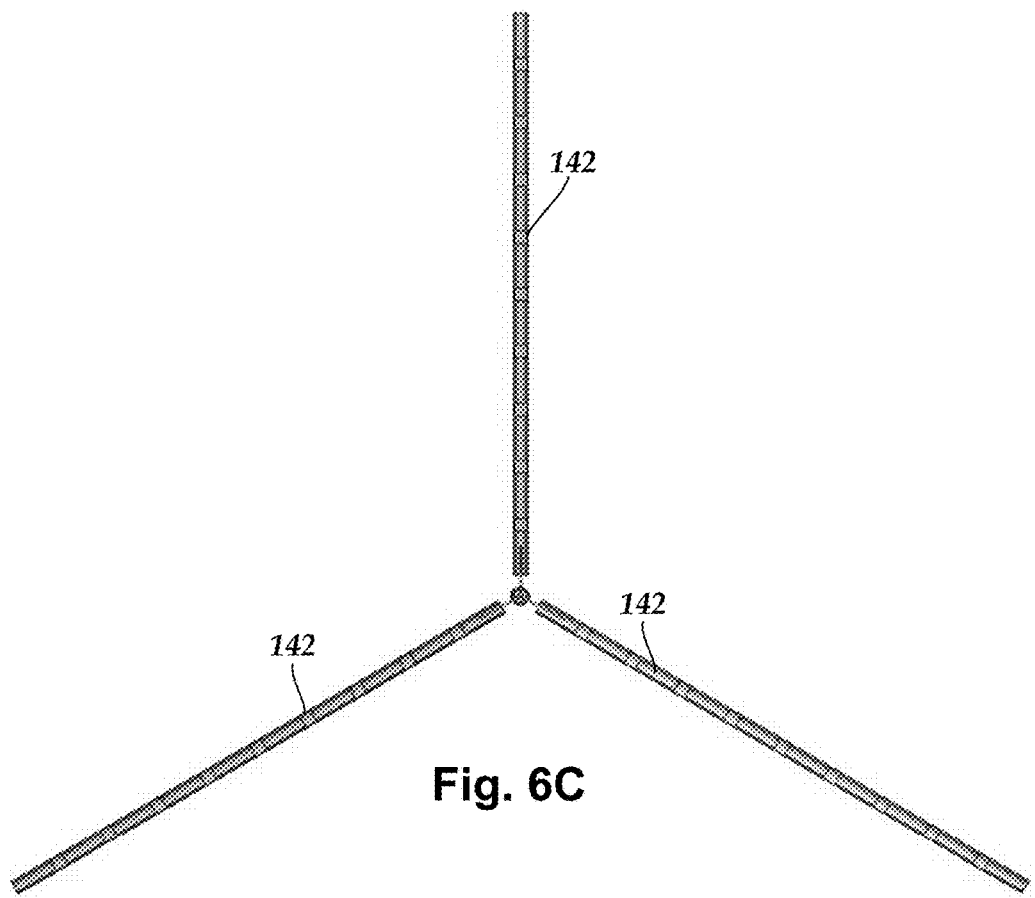
Fig. 6C
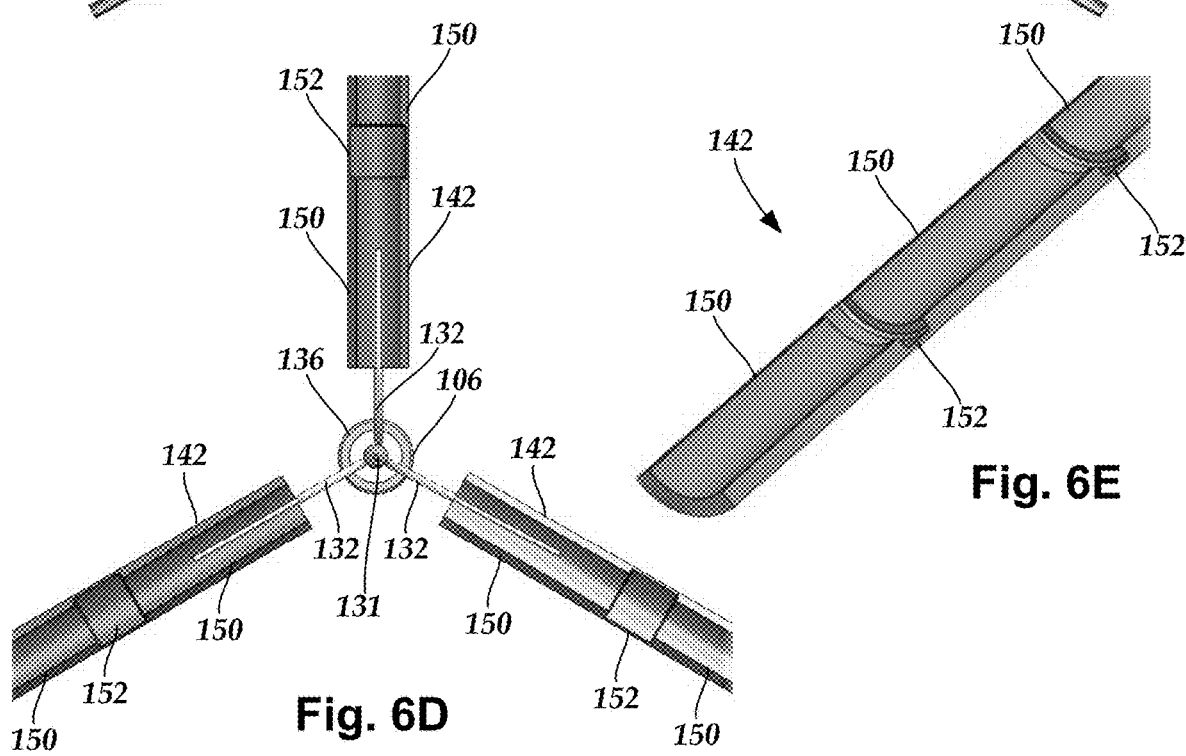
Fig. 6D
Fig. 6E

DIRECTIONAL ELECTRICAL STIMULATION LEADS, SYSTEMS AND METHODS FOR SPINAL CORD STIMULATION

CROSS-REFERENCE TO RELATED APPLICATIONS

This application claims the benefit under 35 U.S.C. § 119(e) of U.S. Provisional Patent Application Ser. No. 62/768,703, filed Nov. 16, 2018, which is incorporated herein by reference.

FIELD

The present disclosure is directed to the area of implantable electrical stimulation systems and methods of making and using the systems. The present disclosure is also directed to directional electrical stimulation leads, systems, and methods for spinal cord stimulation.

BACKGROUND

Implantable electrical stimulation systems have proven therapeutic in a variety of diseases and disorders. For example, spinal cord stimulation systems have been used as a therapeutic modality for the treatment of chronic pain syndromes. Sacral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is an electrical stimulation lead having a proximal portion, a distal portion, and a circumference. The electrical stimulation lead includes terminals disposed along the proximal portion of the electrical stimulation lead; electrodes disposed along the distal portion of the electrical stimulation lead and includes segmented electrodes, where each segmented electrode extends around no more than 75% of the circumference of the lead; conductors electrically coupling the terminals to the electrodes; and an electrode carrier. The electrode carrier includes a center segment, shoulder segments extending from the center segment, and divider segments, each of the divider segments extending from one of the shoulder segments. Each of the divider segments is disposed between, and separates, at least two of the segmented electrodes. A plurality of the segmented electrodes are each disposed on a shoulder of at least one of the shoulder segments.

In at least some aspects, the electrode carrier and the segmented electrodes, in combination, define a plurality of conductor channels bounded by the electrode carrier and the segmented electrodes, wherein each of the conductor channels includes a portion of at least one of the conductors. In at least some aspects, each of the shoulder segments forms two shoulders on opposite sides of the divider segment extending from the shoulder segment. In at least some aspects, the segmented electrodes are each disposed on the shoulder of at least two of the shoulder segments. In at least some aspects, the electrical stimulation lead further includes a lead body disposed over at least part of the electrode carrier. In at least some aspects, the electrode carrier defines a central lumen.

Another aspect is an electrical stimulation lead having a proximal portion, a distal portion, and a circumference. The electrical stimulation lead includes terminals disposed along the proximal portion of the electrical stimulation lead; electrodes disposed along the distal portion of the electrical stimulation lead and includes segmented electrodes, where each segmented electrode extends around no more than 75% of the circumference of the lead; conductors electrically coupling the terminals to the electrodes; and an electrode carrier. The electrode carrier includes a center segment and a plurality of rails, each of the rails extending from the center segment. A portion of each of the rails is disposed between, and separates, at least two of the segmented electrodes. The electrode carrier and the segmented electrodes, in combination, define a plurality of conductor channels bounded by the electrode carrier and the segmented electrodes, where each of the conductor channels includes a portion of at least one of the conductors.

In at least some aspects, each of the segmented electrodes is disposed on a portion of at least one of the rails of the electrode carrier. In at least some aspects, each of the rails includes a shoulder segment and a divider segment disposed on the should segment, where each of the shoulder segments forms two shoulders on opposite sides of the divider segment of the rail. In at least some aspects, the segmented electrodes are each disposed on the shoulder of at least two of the shoulder segments. In at least some aspects, the electrical stimulation lead further includes a lead body disposed over at least part of the electrode carrier. In at least some aspects, the electrode carrier defines a central lumen.

Yet another aspect is a system for electrical stimulation that includes any of the electrical stimulation leads described above and a control module electrically coupleable to the electrical stimulation lead.

A further aspect is a method of making an electrical stimulation lead. The method includes disposing a plurality of electrode strips on an electrode carrier, each of the electrode strips including a plurality of pre-electrodes and at least one connection region in an alternating, longitudinal arrangement with one of the at least one connection region disposed between each adjacent pair of the pre-electrodes of the electrode strip; and removing each of the at least one connection region of each of the electrode strips to separate the pre-electrodes into segmented electrodes.

In at least some aspects, the method further includes attaching a conductor to each of the pre-electrodes of each of the electrode strips prior to disposing the electrode strips on the electrode carrier. In at least some aspects, the method further includes, after disposing the electrode strips on the electrode carrier, disposing a sleeve over the electrode strips and injecting a non-conductive material into the sleeve to form a portion of a lead body between the pre-electrodes. In at least some aspects, injecting the non-conductive material includes injecting the non-conductive material into carrier channels defined by the electrode strips and the electrode carrier.

In at least some aspects, the method further includes disposing at least one ring electrode and at least one spacer on the electrical stimulation lead before or after disposing the electrode strips on the electrode carrier. In at least some aspects, disposing the electrode strips includes disposing the electrode strips parallel to each other and to a longitudinal axis of the electrode carrier. In at least some aspects, disposing the electrode strips includes disposing the electrode strips on the electrode carrier with a divider segment of the electrode carrier separating each adjacent pair of the electrode strips.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic perspective view of a portion of one embodiment of a lead with thirty-two electrodes;

FIG. 4B is a schematic perspective view of portions of one embodiment of a lead with sixteen electrodes;

FIG. 4C is a schematic perspective view of portions of another embodiment of a lead with sixteen electrodes;

FIG. 4D is a schematic perspective view of portions of a third embodiment of a lead with sixteen electrodes;

FIG. 4E is a schematic perspective view of a portion of another embodiment of a lead with thirty-two electrodes;

FIG. 6C is a schematic end view of a portion of the arrangement of FIG. 6B with three electrode strips added;

FIG. 6D is a close-up view of a central portion of the arrangement of FIG. 6C;

FIG. 6E is a schematic perspective view of a portion of an electrode strip;

DETAILED DESCRIPTION

The present disclosure is directed to the area of implantable electrical stimulation systems and methods of making and using the systems. The present disclosure is also directed to directional electrical stimulation leads, systems, and methods for spinal cord stimulation.

Suitable implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 1:
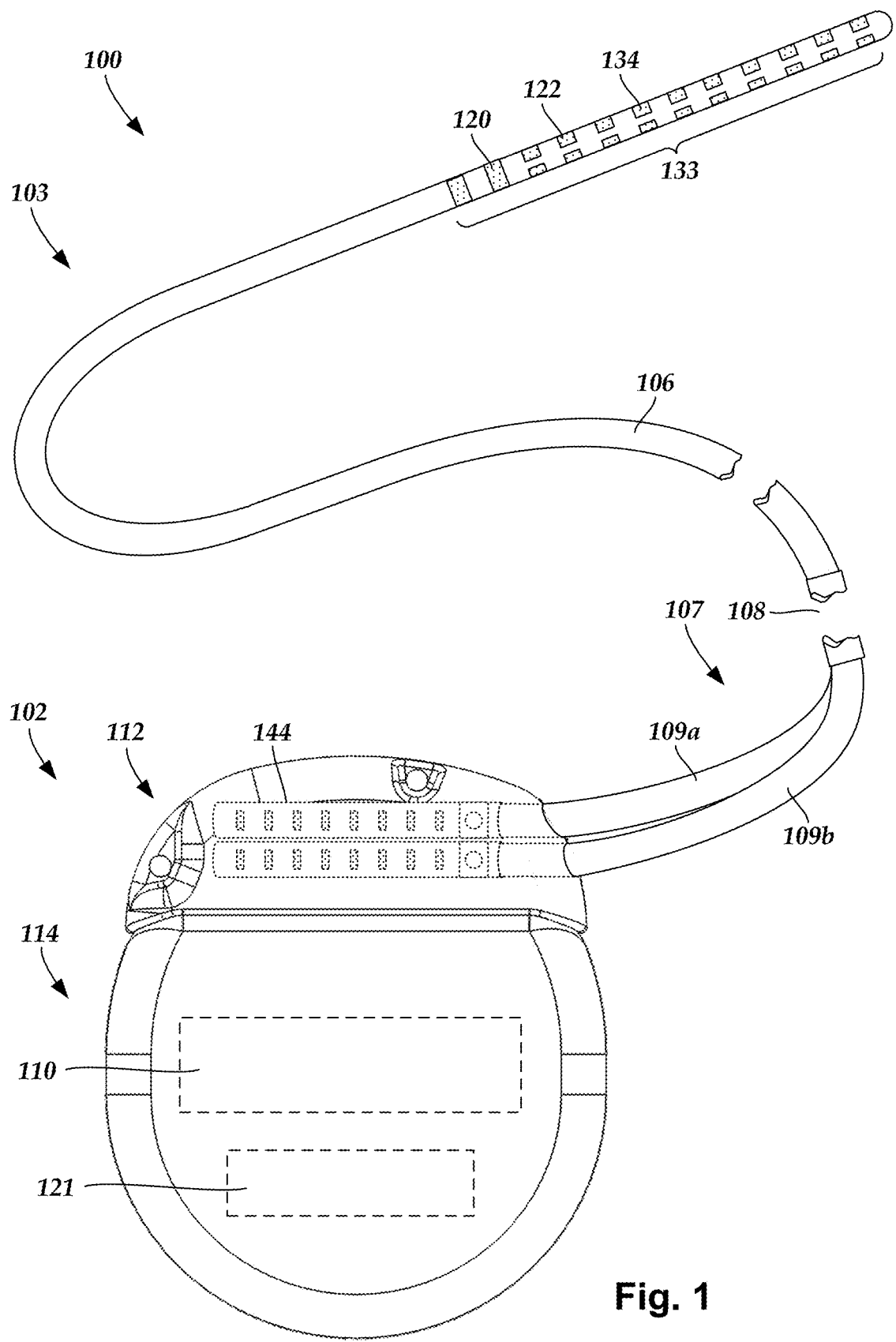
FIG. 1 is a schematic view of another embodiment of an electrical stimulation system that includes a percutaneous lead body coupled to a control module.

FIG. 1 illustrates schematically one embodiment of an electrical stimulation system 100. The electrical stimulation system includes a control module (e.g., a stimulator or pulse generator) 102 and at least one lead 103 coupleable to the control module 102. The lead 103 includes one or more lead bodies 106, an array of electrodes 133, such as electrode 134, and an array of terminals (e.g., 210 in FIG. 2-3) disposed along the one or more lead bodies 106. In at least some embodiments, the lead is isodiametric along a longitudinal length of the lead body 106. FIG. 1 illustrates one lead 103 coupled to a control module 102. Other embodiments may include two, three, four, or more leads 103 coupled to the control module 102.

The lead 103 can be coupled to the control module 102 in any suitable manner. In at least some embodiments, the lead 103 couples directly to the control module 102. In at least some other embodiments, the lead 103 couples to the control module 102 via one or more intermediate devices. For example, in at least some embodiments one or more lead extensions 224 (see e.g., FIG. 3) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109*a* and 109*b* configured and arranged to couple to the control module 102 (or another splitter, a lead extension, an adaptor, or the like).

The control module 102 typically includes a connector housing 112 and a sealed electronics housing 114. An electronic subassembly 110 and an optional power source 121 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2:
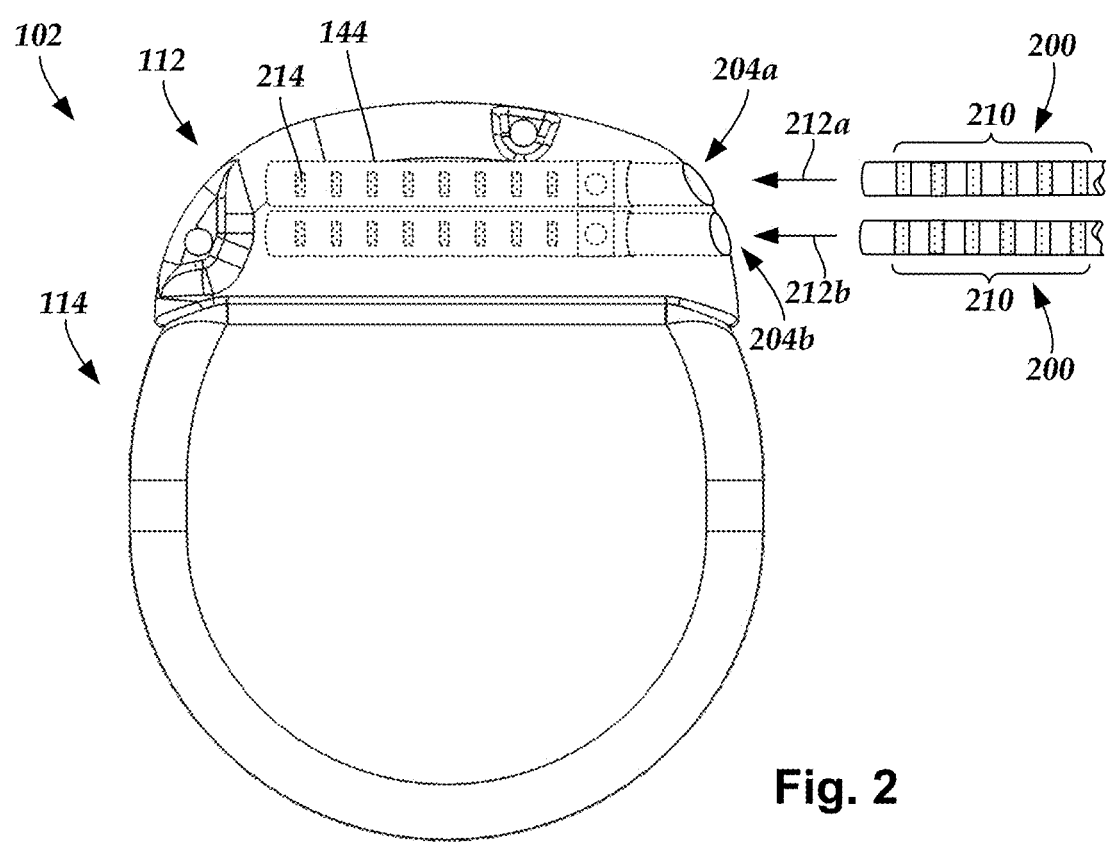
FIG. 2 is a schematic view of one embodiment of a plurality of connector assemblies disposed in the control module of FIG. 1A, the connector assemblies configured and arranged to receive the proximal portions of the lead bodies of FIG. 1A.
Figure 3:
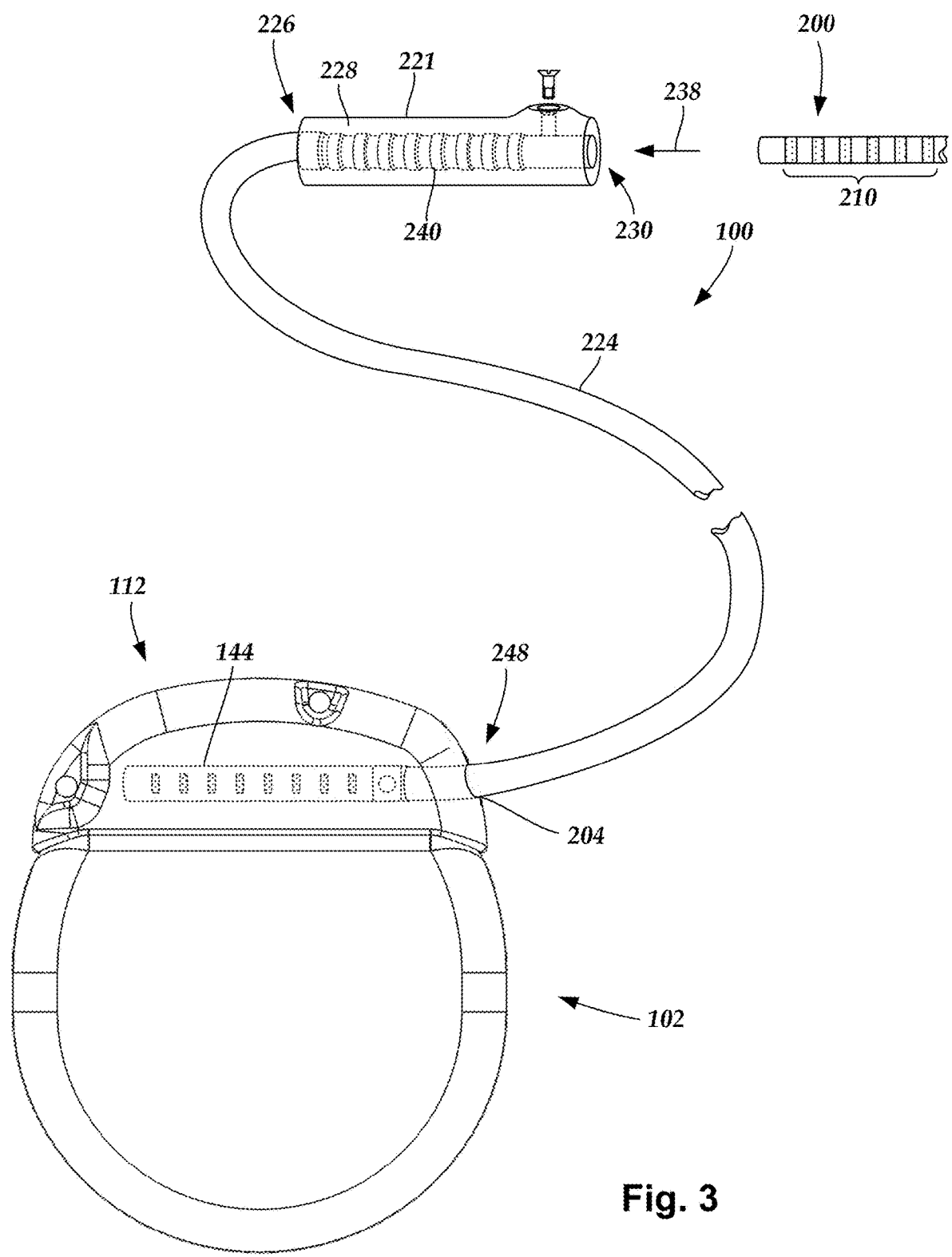
FIG. 3 is a schematic view of one embodiment of a proximal portion of the lead body of FIG. 1, a lead extension, and the control module of FIG. 1A, the lead extension configured and arranged to couple the lead body to the control module.

Terminals (e.g., 210 in FIGS. 2-3) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIGS. 2 and 240 in FIG. 3). The connector contacts are disposed in connectors (e.g., 144 in FIGS. 1-3; and 221 in FIG. 3) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2 is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 3, an adaptor, or the like or combinations thereof), or a combination thereof. FIG. 2 illustrates two elongated devices 200 coupled to the control module 102. These two elongated devices 200 can be two tails as illustrated in FIG. 1 or two different leads or any other combination of elongated devices.

The control module connector 144 defines at least one port into which a proximal end of the elongated device 200 can be inserted, as shown by directional arrows 212*a* and 212*b*. In FIG. 2 (and in other figures), the connector housing 112 is shown having two ports 204*a* and 204*b*. The connector housing 112 can define any suitable number of ports including, for example, one, two, three, four, five, six, seven, eight, or more ports.

The control module connector 144 also includes a plurality of connector contacts, such as connector contact 214, disposed within each port 204*a* and 204*b*. When the elongated device 200 is inserted into the ports 204*a* and 204*b*, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference in their entireties.

FIG. 3 is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 3, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 221 is disposed on the lead extension 224. In FIG. 3, the lead extension connector 221 is shown disposed at a distal end 226 of the lead extension 224. The lead extension connector 221 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 3), the proximal end 248 of the lead extension 224 is configured and arranged for insertion into the control module connector 144.

Returning to FIG. 1, at least some of the stimulation electrodes take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

In FIG. 1, the electrodes 134 are shown as including both ring electrodes 120 and segmented electrodes 122. In some embodiments, the electrodes 134 are all segmented. The segmented electrodes 122 of FIG. 1 are in sets of three (one of which is not visible in FIG. 1), where the three segmented electrodes of a particular set are electrically isolated from one another and are circumferentially offset along the lead 1-3. Any suitable number of segmented electrodes can be formed into a set including, for example, two, three, four, or more segmented electrodes. The lead 103 of FIG. 1 has thirty segmented electrodes 122 (ten sets of three electrodes each) and two ring electrodes 120 for a total of 32 electrodes 134.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

Examples of leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. A lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

FIG. 4A illustrates a 32-electrode lead 103 with a lead body 106 and two ring electrodes 120 proximal to thirty segmented electrodes 122 arranged in ten sets of three segmented electrodes each. In the illustrated embodiments, the ring electrodes 120 are proximal to the segmented electrodes 122. In other embodiments, the ring electrodes 120 can be proximal to, or distal to, or any combination thereof.

Any number of segmented electrodes 122 may be disposed on the lead body including, for example, one, two, three, four, five, six, seven, eight, nine, ten, eleven, twelve, thirteen, fourteen, fifteen, sixteen, twenty, twenty-four, twenty-eight, thirty, thirty-two, or more segmented electrodes 122. It will be understood that any number of segmented electrodes 122 may be disposed along the length of the lead body. A segmented electrode 122 typically extends only 75%, 67%, 60%, 50%, 40%, 33%, 25%, 20%, 17%, 15%, or less around the circumference of the lead.

The segmented electrodes 122 may be grouped into sets of segmented electrodes, where each set is disposed around a circumference of the lead 103 at a particular longitudinal portion of the lead 103. The lead 103 may have any number of segmented electrodes 122 in a given set of segmented electrodes. The lead 103 may have one, two, three, four, five, six, seven, eight, or more segmented electrodes 122 in a given set. The lead 103 may have any number of sets of segmented electrodes including, but not limited to, one, two, three, four, five, six, eight, ten, twelve, fifteen, sixteen, twenty, or more sets. The segmented electrodes 122 may be uniform, or vary, in size and shape. In some embodiments, the segmented electrodes 122 are all of the same size, shape, diameter, width or area or any combination thereof. In some embodiments, the segmented electrodes 122 of each circumferential set (or even all segmented electrodes disposed on the lead 103) may be identical in size and shape.

Each set of segmented electrodes 122 may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the lead 103. In at least some embodiments, equal spaces, gaps or cutouts are disposed between each segmented electrode 122 around the circumference of the lead body. In other embodiments, the spaces, gaps or cutouts between the segmented electrodes 122 may differ in size or shape. In other embodiments, the spaces, gaps, or cutouts between segmented electrodes 122 may be uniform for a particular set of the segmented electrodes 122, or for all sets of the segmented electrodes 122. The sets of segmented electrodes 122 may be positioned in irregular or regular intervals along a length of the lead body.

The electrodes of the lead 103 are typically disposed in, or separated by, a non-conductive, biocompatible material of a lead body 106 including, for example, silicone, polyurethane, and the like or combinations thereof. The lead body 106 may be formed in the desired shape by any process including, for example, extruding, molding (including injection molding), casting, and the like. Electrodes and connecting wires can be disposed onto or within a lead body either prior to or subsequent to a molding or casting process. The non-conductive material typically extends from the distal end of the lead body 106 to the proximal end of the lead body 106.

FIG. 4B to 4E illustrate other embodiments of leads with segmented electrodes 122. FIG. 4B illustrates a sixteen electrode lead 103 having one ring electrode 120 that is proximal to five sets of three segmented electrodes 122 each. FIG. 4C illustrates a sixteen electrode lead 103 having eight sets of two segmented electrodes 122 each. As illustrated in FIG. 4C, an embodiment of a lead 103 does not necessarily include a ring electrode. FIG. 4D illustrates a sixteen electrode lead 103 having four ring electrodes 120 that are proximal to six sets of two segmented electrodes 122 each. FIG. 4E illustrates a thirty-two electrode lead 103 having sixteen sets of two segmented electrodes 122 each (for clarity of illustration, not all of the electrodes are shown). It will be recognized that any other electrode combination of ring electrodes, segmented electrodes, or both types of electrodes can be used.

FIGS. 5A-5G illustrate additional leads 103 with segmented electrodes 122, optional ring electrodes 120 or tip stimulators 125, and a lead body 106. The sets of segmented electrodes 122 each include either two (FIG. 5B), three (FIGS. 5F and 5G), or four (FIGS. 5A and 5C-5E) or any other number of segmented electrodes including, for example, five, six, or more.

When the lead 103 includes both ring electrodes 120 and segmented electrodes 122, the ring electrodes 120 and the segmented electrodes 122 may be arranged in any suitable configuration. For example, when the lead 103 includes two ring electrodes 120 and two sets of segmented electrodes 122, the ring electrodes 120 can flank the two sets of segmented electrodes 122 (see e.g., FIGS. 5A and 5F). Alternately, the two sets of ring electrodes 120 can be disposed proximal to the two sets of segmented electrodes 122 (see e.g., FIG. 5C), or the two sets of ring electrodes 120 can be disposed distal to the two sets of segmented electrodes 122 (see e.g., FIG. 5D). The lead may also include a tip stimulator (see, tip stimulator 125 of FIGS. 5E and 5G). It will be understood that other configurations are possible as well (e.g., alternating ring and segmented electrodes, or the like).

By varying the location of the segmented electrodes 122, different coverage of the target neurons may be selected. For example, the electrode arrangement of FIG. 5C may be useful if the physician anticipates that the neural target will be closer to a distal tip of the lead body 106, while the electrode arrangement of FIG. 5D may be useful if the physician anticipates that the neural target will be closer to a proximal end of the lead body 106.

Figure 5A:
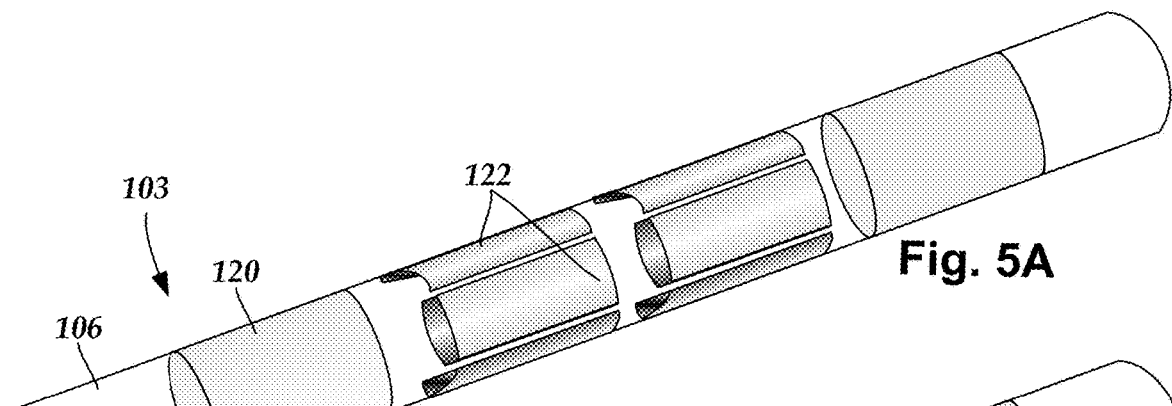
FIG. 5A is a schematic perspective view of a portion of one embodiment of a lead with ten electrodes.
Figure 5B:
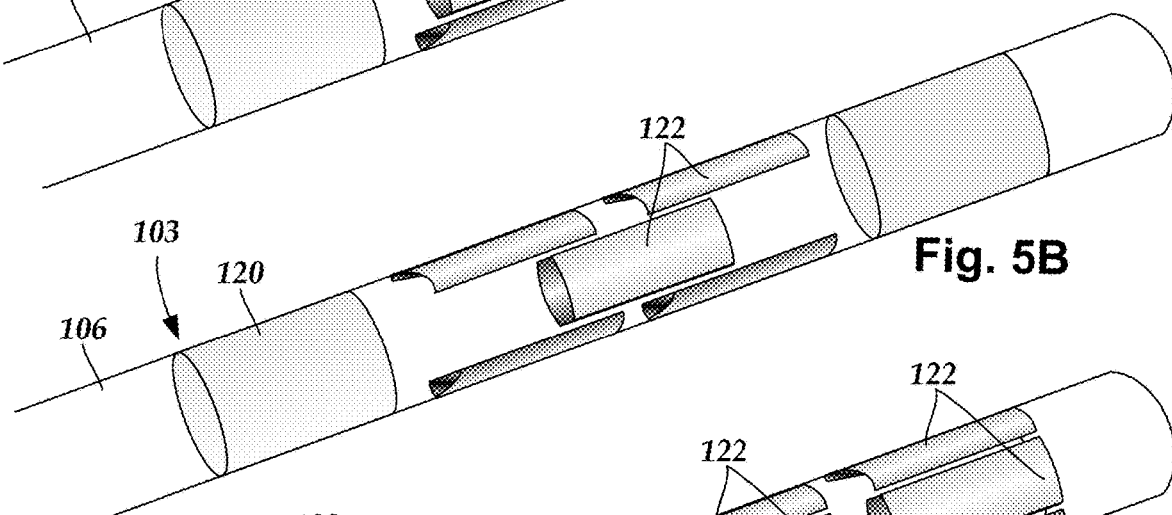
FIG. 5B is a schematic perspective view of portions of one embodiment of a lead with eight electrodes.
Figure 5C:
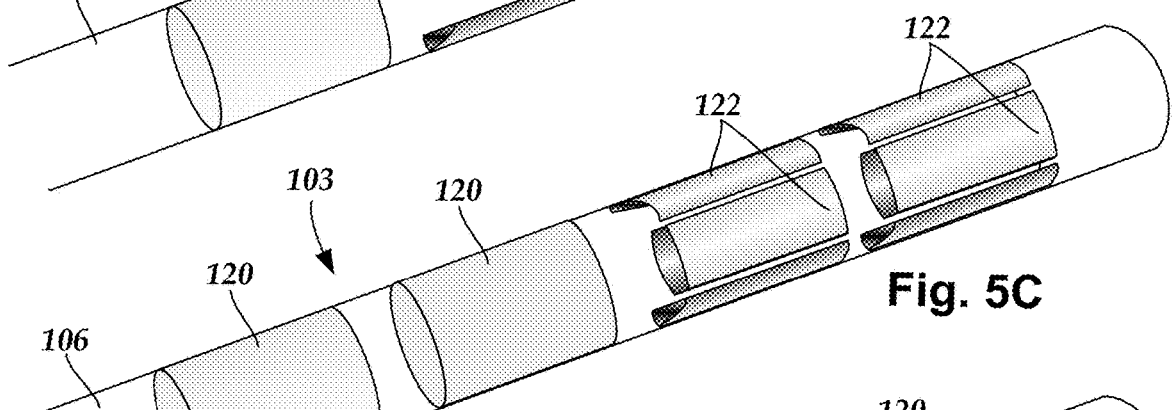
FIG. 5C is a schematic perspective view of portions of another embodiment of a lead with ten electrodes.
Figure 5D:
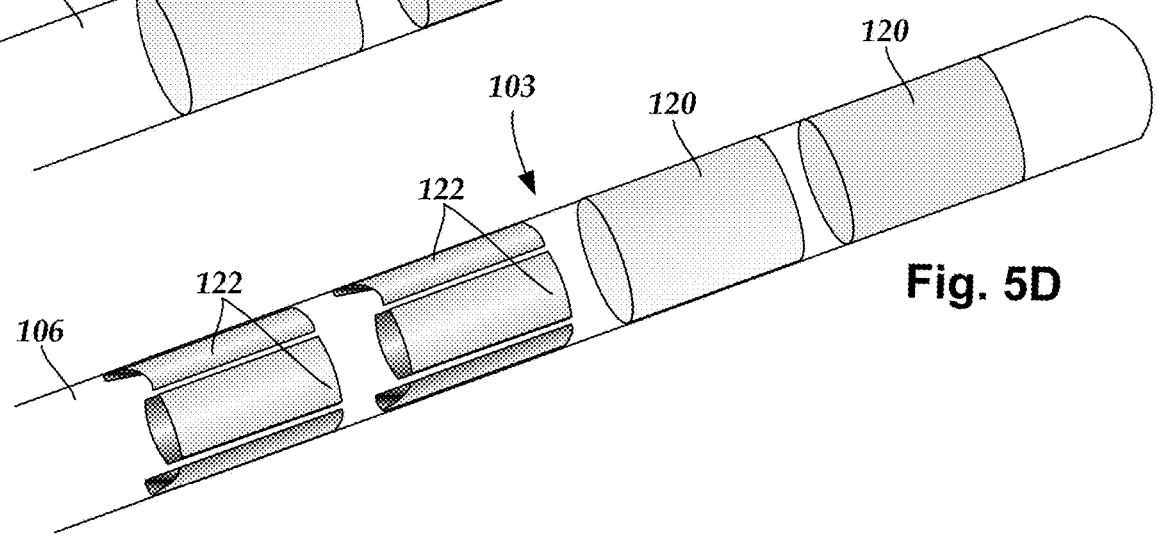
FIG. 5D is a schematic perspective view of portions of a third embodiment of a lead with ten electrodes.
Figure 5E:
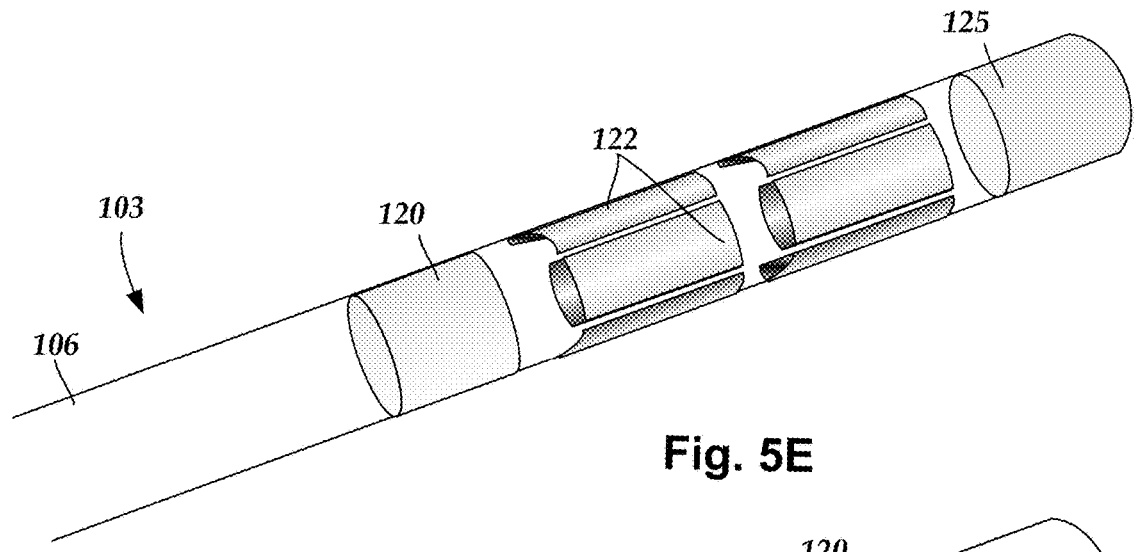
FIG. 5E is a schematic perspective view of a portion of a fourth embodiment of a lead with ten electrodes.
Figure 5F:
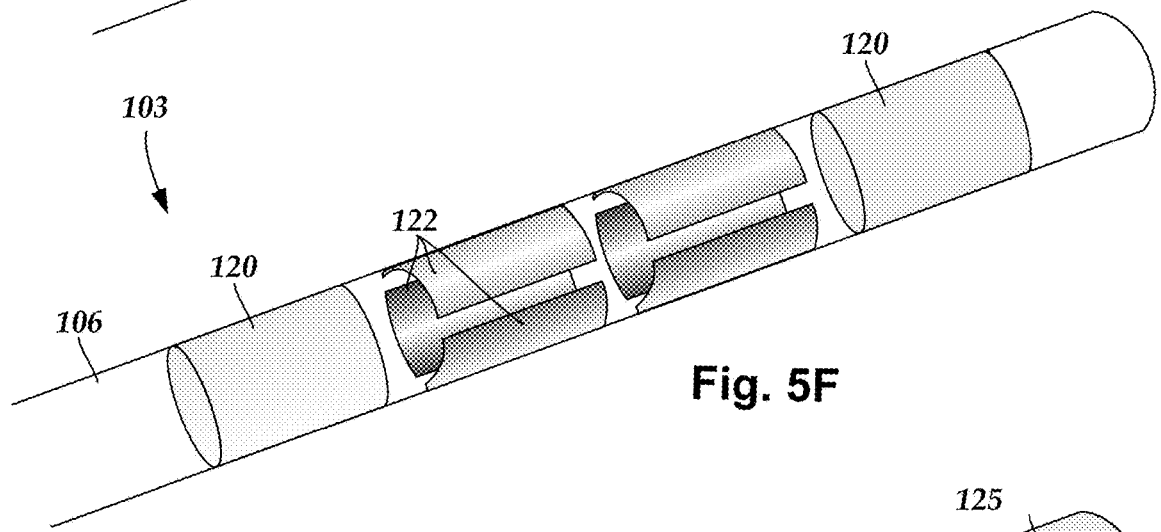
FIG. 5F is a schematic perspective view of a portion of another embodiment of a lead with eight electrodes.
Figure 5G:
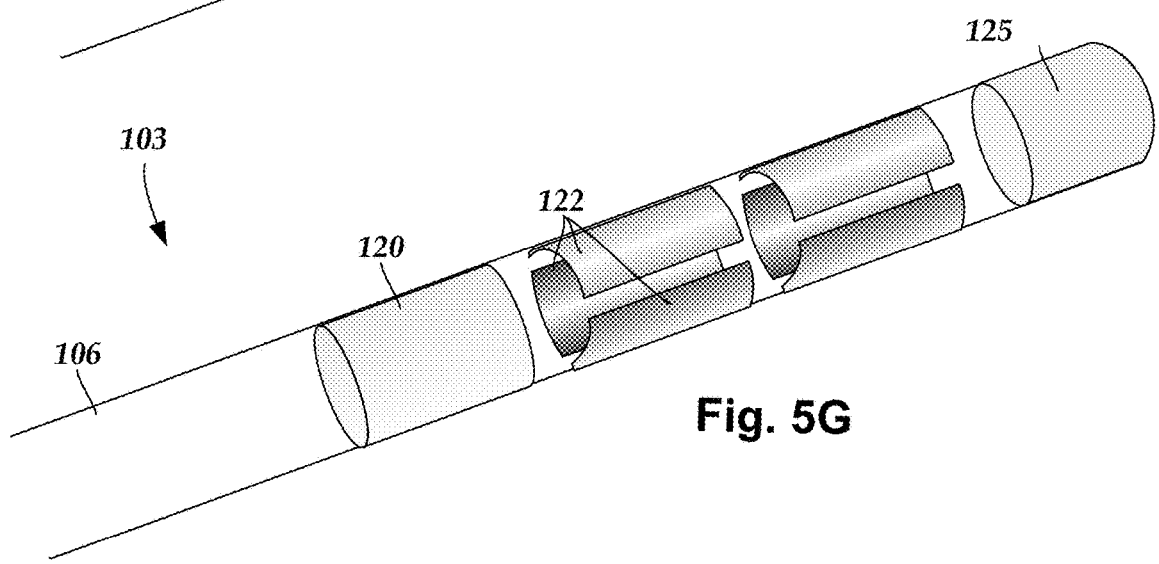
FIG. 5G is a schematic perspective view of portions of a third embodiment of a lead with eight electrodes.

Any combination of ring electrodes 120 and segmented electrodes 122 may be disposed on the lead 103. For example, the lead may include a first ring electrode 120, two sets of segmented electrodes; each set formed of four segmented electrodes 122, and a final ring electrode 120 at the end of the lead. This configuration may simply be referred to as a 1-4-4-1 configuration (FIG. 5A). It may be useful to refer to the electrodes with this shorthand notation. Thus, the embodiment of FIG. 5C may be referred to as a 1-1-4-4 configuration, while the embodiment of FIG. 5D may be referred to as a 4-4-1-1 configuration. The embodiments of FIG. 5G can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 122 are disposed on the lead. The 1-3-3-1 electrode configuration of FIG. 5G has two sets of segmented electrodes, each set containing three electrodes disposed around the perimeter of the lead, flanked by two ring electrodes. In some embodiments, the lead includes 16 electrodes. Possible configurations for a 16-electrode lead include, but are not limited to 4-4-4-4; 6-8; 5-3-3-3-3-1 (and all rearrangements of this configuration); and 2-2-2-2-2-2-2-2. Any other suitable segmented electrode arrangements (with or without ring electrodes) can be used including, but not limited to, those disclosed in U.S. Provisional Patent Application Ser. No. 62/113,291 and U.S. Patent Applications Publication Nos. 2012/0197375 and 2015/0045864, all of which are incorporated herein by reference in their entirety.

In some embodiments, a tip stimulator 125 is a tip electrode. In other embodiments, the tip stimulator 125 can be an optical stimulator, such as a LED, OLED, laser diode, or other light emitter or a tip of an optical fiber or other optical waveguide from which light can be emitted. In addition to the tip stimulator 125, the lead 103 may also include ring electrodes, segmented electrodes, or both types of electrodes. For example, the lead 103 can include six, eight, ten, twelve, fourteen, sixteen, eighteen, twenty, twenty-two, twenty-four, or thirty electrodes and an optical tip stimulator. As other examples, the lead can include a tip stimulator and either a) thirty ring electrodes, b) twelve sets of two segmented electrodes each and six ring electrodes, or c) six sets of two segmented electrodes each and two ring electrodes.

The electrodes 120, 122 may have any suitable longitudinal length including, but not limited to, 2, 3, 4, 4.5, 5, or 6 mm. The longitudinal spacing between adjacent electrodes 120, 122 (as well as between an adjacent electrode 120, 122 and tip stimulator 125) may be any suitable amount including, but not limited to, 1, 2, or 3 mm, where the spacing is defined as the distance between the nearest edges of two adjacent electrodes. In some embodiments, the spacing is uniform between longitudinally adjacent of electrodes along the length of the lead. In other embodiments, the spacing between longitudinally adjacent electrodes may be different or non-uniform along the length of the lead.

Figure 6A:
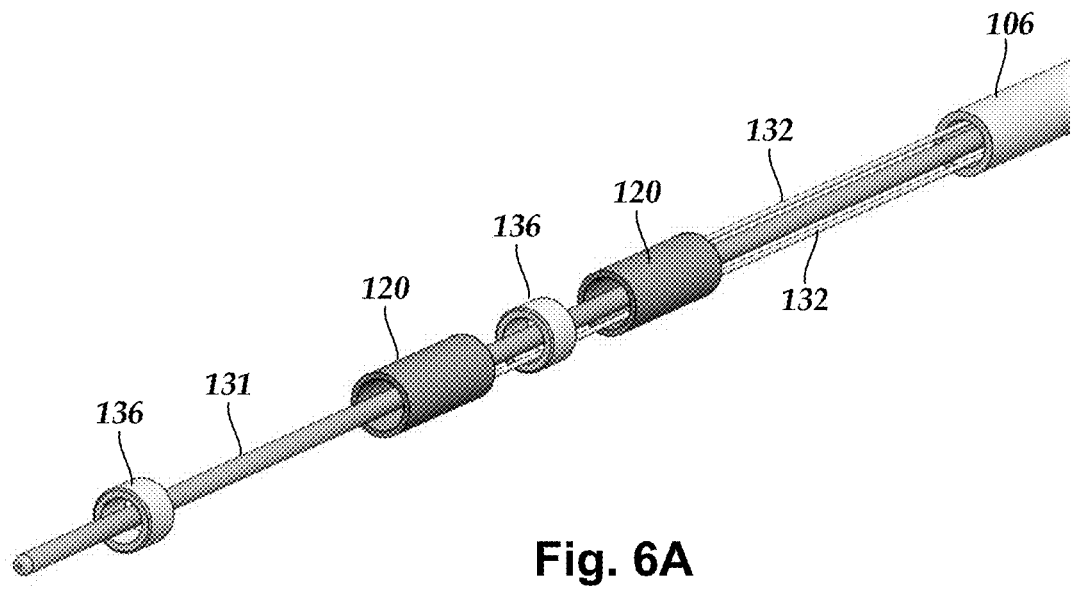
FIG. 6A is a schematic perspective view of a portion of a lead body with two spacers and two ring electrodes.
Figure 6B:
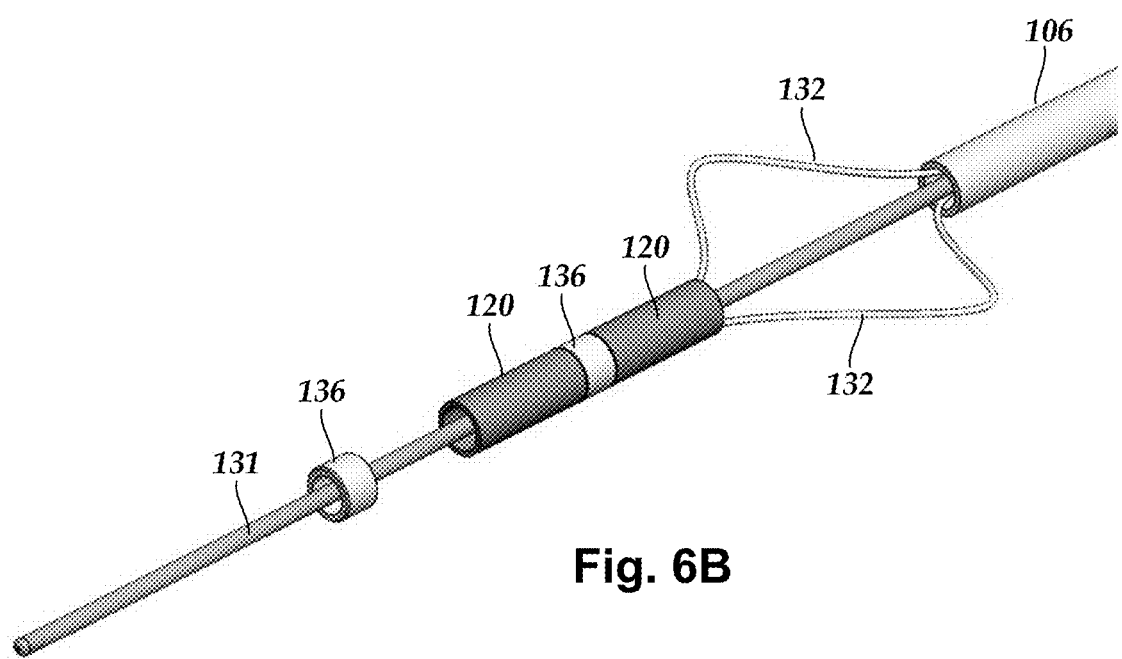
FIG. 6B is a schematic perspective view of the lead body, spacers, and ring electrodes of FIG. 6A with the ring electrodes and one spacer pushed together.
Figure 6F:
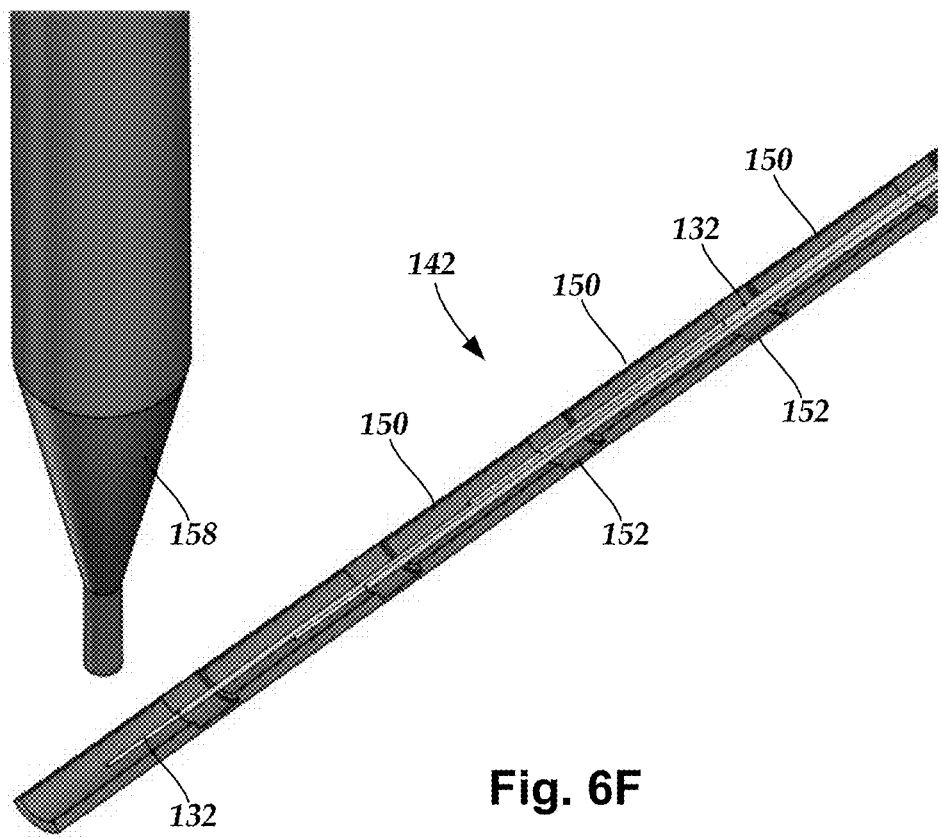
FIG. 6F is schematic perspective view of attachment of a conductor to a pre-electrode on the electrode strip of FIG. 6E.
Figure 6G:
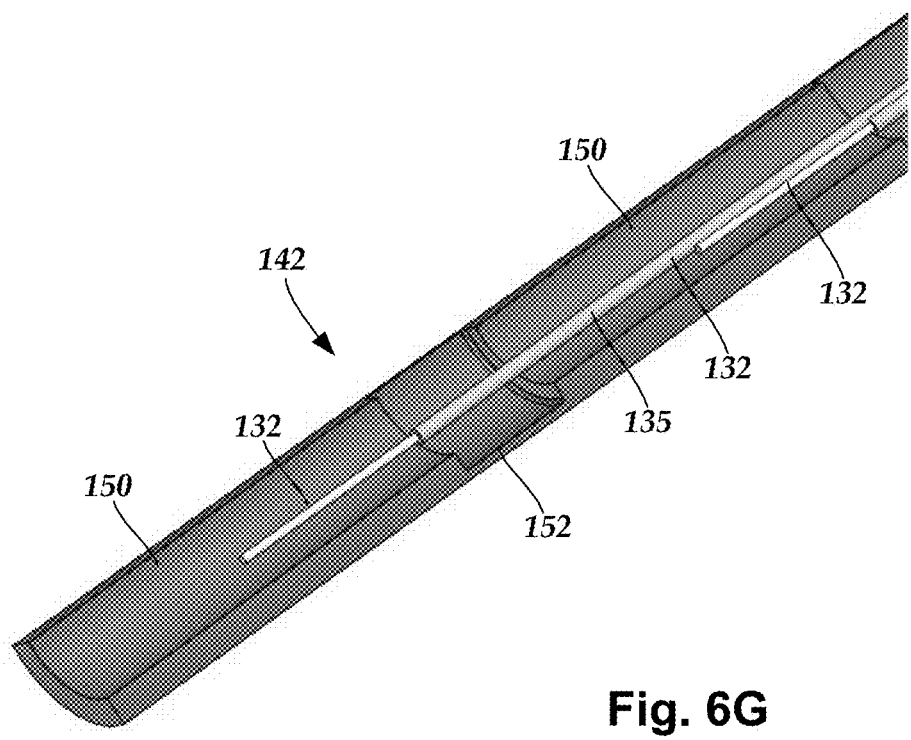
FIG. 6G is a schematic perspective view of conductors attached to pre-electrodes on the electrode strip of FIG. 6E.
Figure 6H:
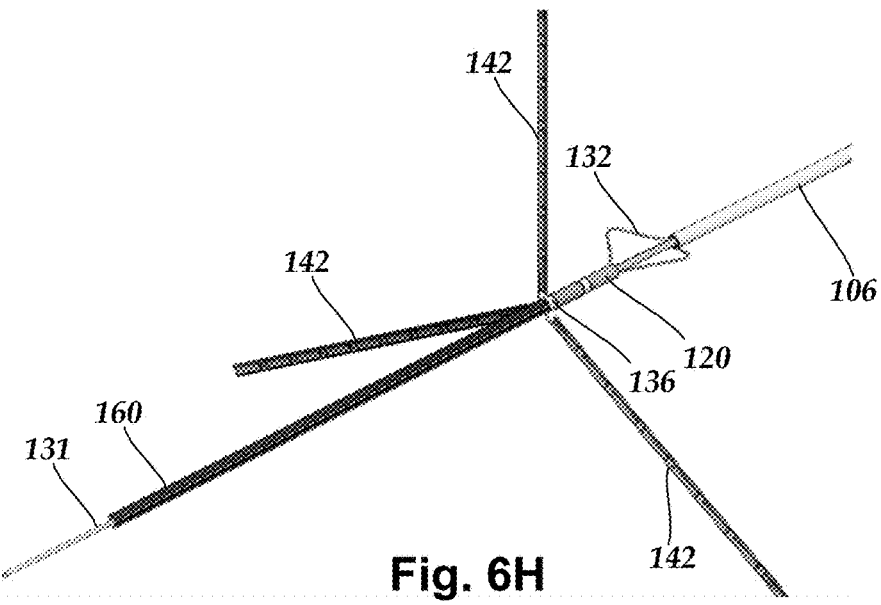
FIG. 6H is a schematic perspective view of the arrangement of FIG. 6C with an electrode carrier added.
Figure 6I:
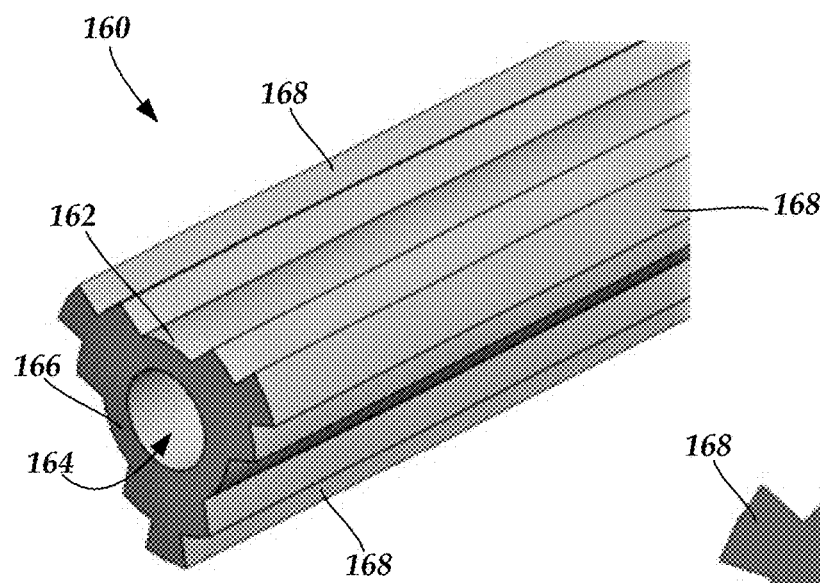
FIG. 6I is a schematic perspective view of a portion of an electrode carrier.
Figure 6J:
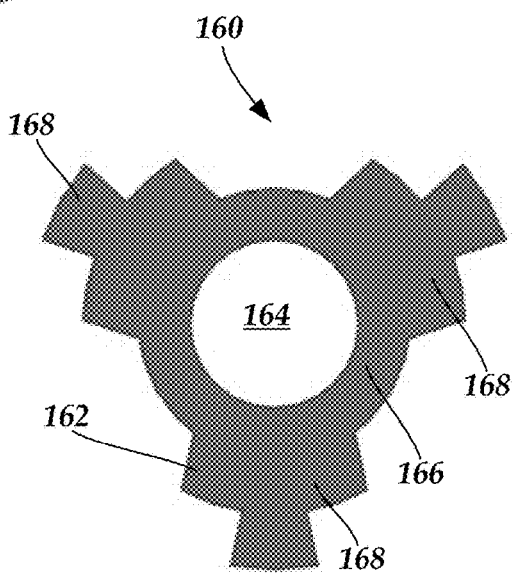
FIG. 6J is a schematic cross-sectional view of the electrode carrier of FIG. 6I.
Figure 6K:
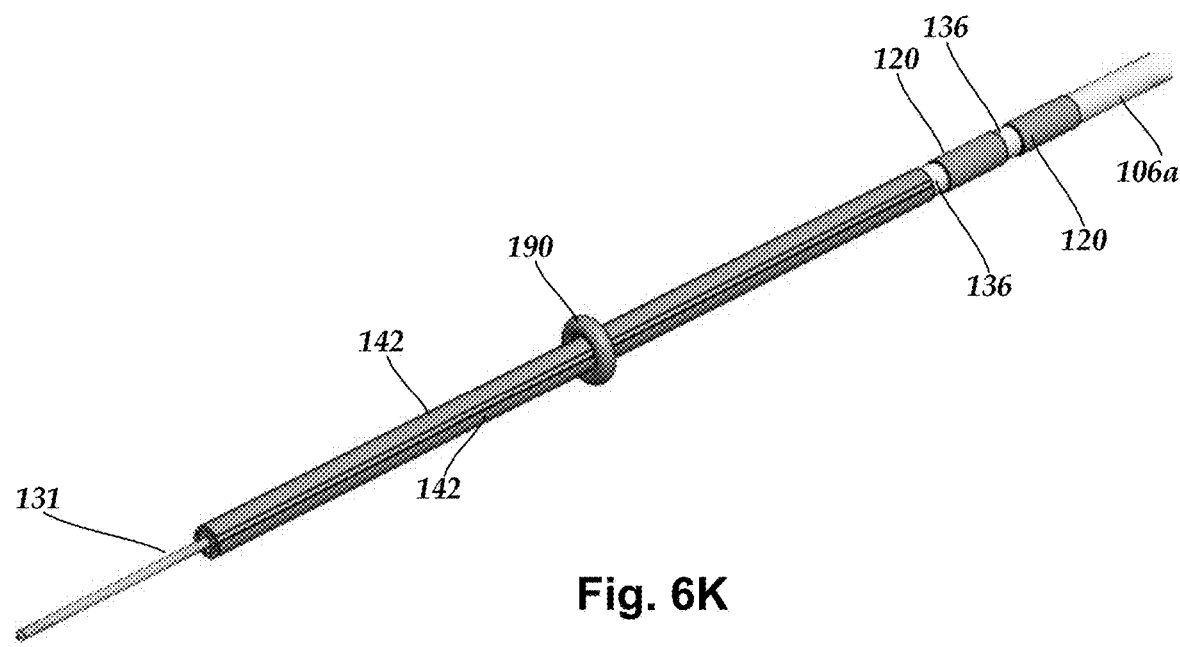
FIG. 6K is a schematic perspective view of the arrangement of FIG. 6H with the electrode strips disposed against the electrode carrier.
Figure 6L:
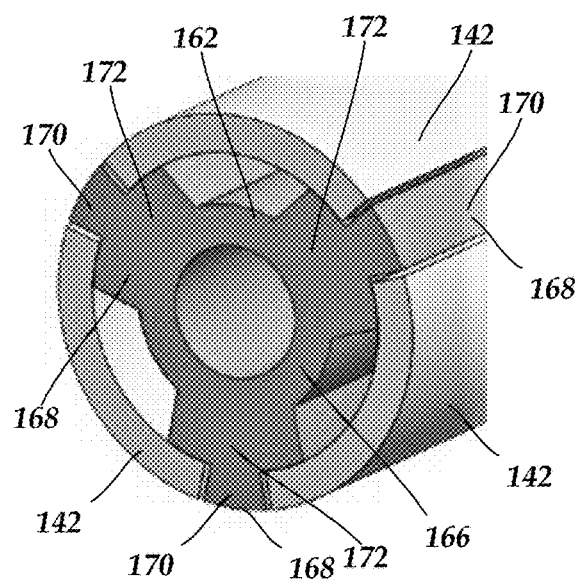
FIG. 6L is a close-up view of portions of electrode strips disposed on an electrode carrier.
Figure 6M:
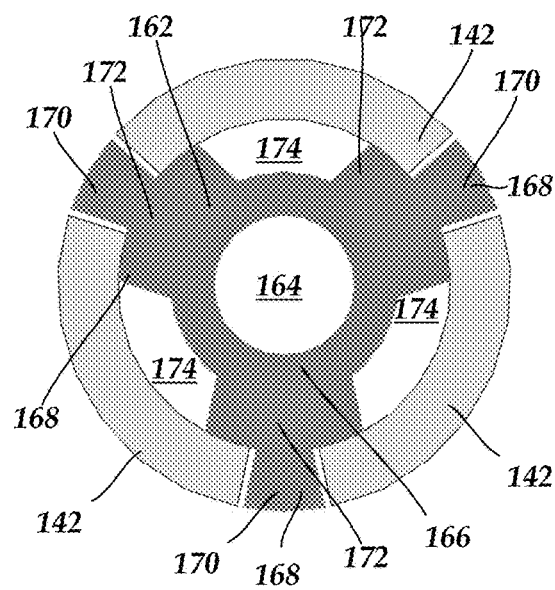
FIG. 6M is a schematic cross-sectional view of the arrangement of FIG. 6L.
Figure 6N:
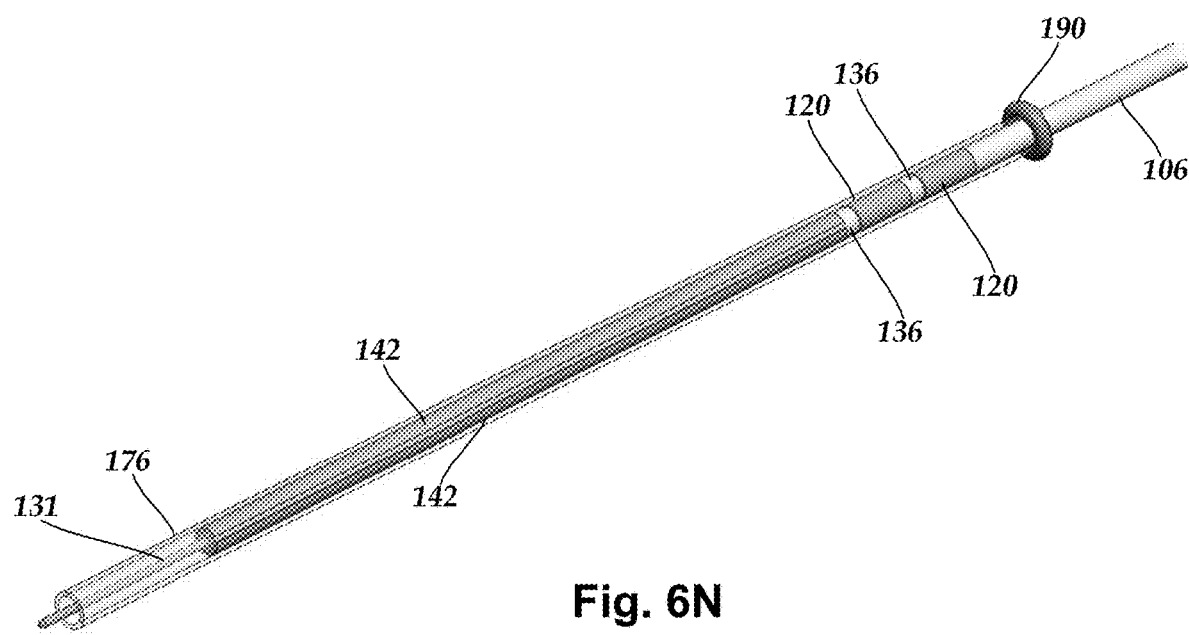
FIG. 6N is a schematic perspective view of the arrangement of FIG. 6K with a sleeve added.
Figure 6O:
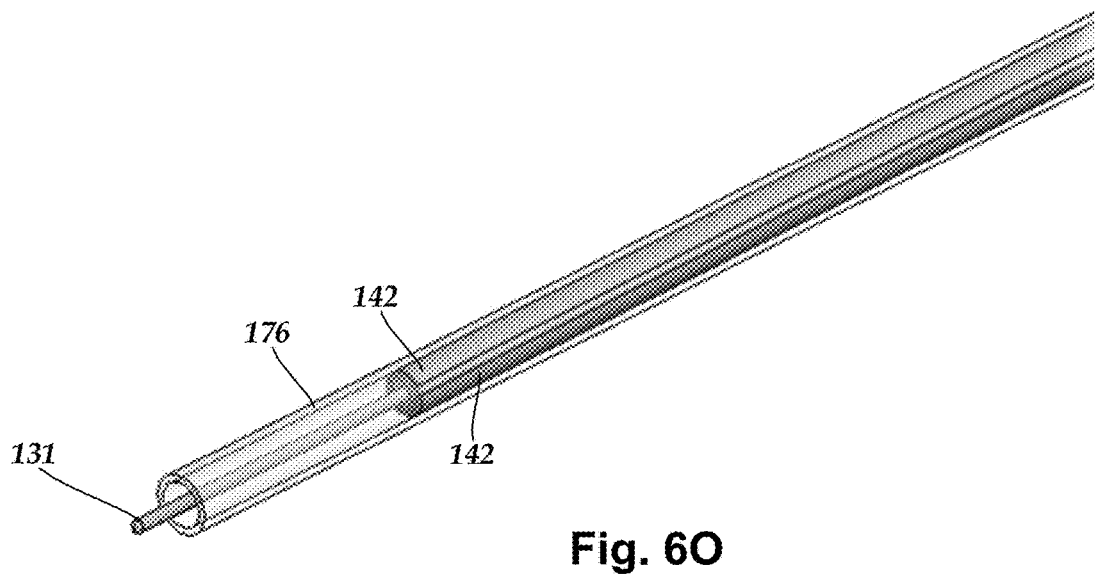
FIG. 6O is a close-up view of a portion of the arrangement of FIG. 6N.
Figure 6P:
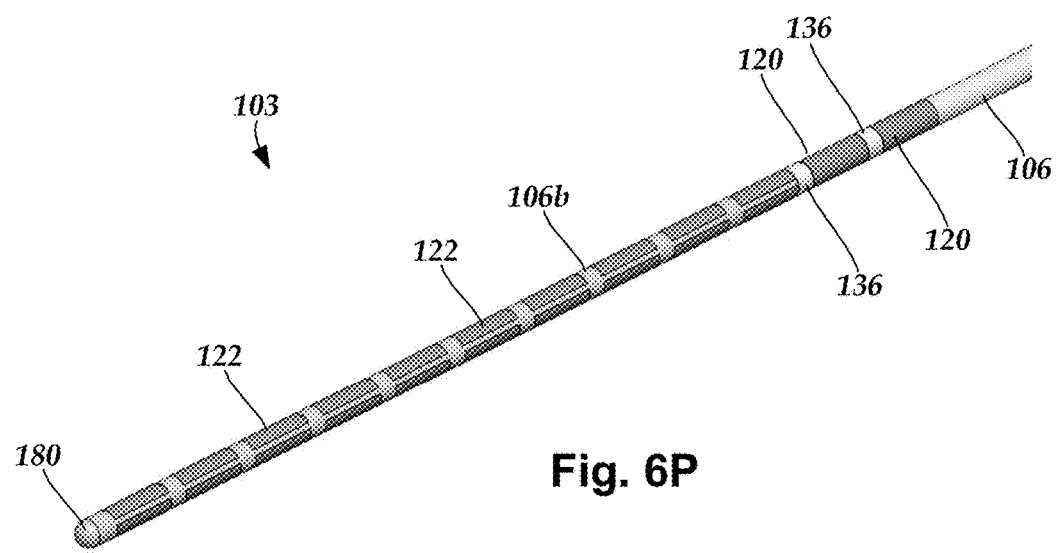
FIG. 6P is a schematic perspective view of the arrangement of FIG. 6N after grinding to release the segmented electrodes.
Figure 6Q:
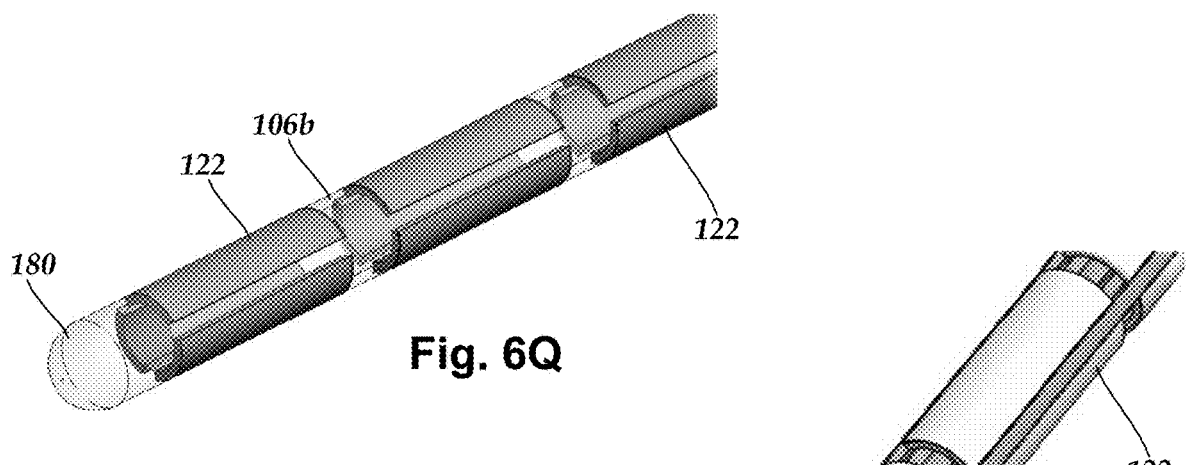
FIG. 6Q is a close-up view of a portion of the lead of FIG. 6P.
Figure 6R:
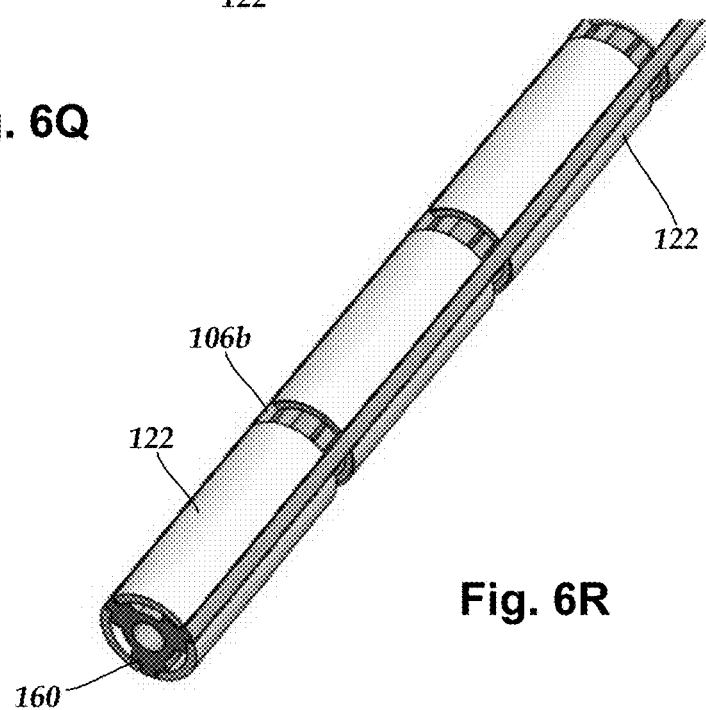
FIG. 6R is a close-up view of a portion of the arrangement of FIG. 6P with the electrode carrier visible and a portion of the lead body transparent to view the electrode carrier.

FIGS. 6A to 6R illustrate steps in one embodiment of a method for making a lead with segmented electrodes. FIG. 6A illustrates a portion of a lead body 106 with conductors 132 and a temporary mandrel 131 extending out of the lead body. Two ring electrodes 120 and two spacers 136 are disposed around the mandrel 131. The two ring electrodes 120 are individually attached to a different one of the conductors 132. The spacers are made of a non-conductive material such as, but not limited to, silicone or polyurethane. In FIG. 6B, the ring electrodes 120 and a spacer 136 between the ring electrodes are brought together. In at least some embodiments, slack is created in the conductors 132 between the ring electrodes 120 and the lead body 106, as illustrated in FIG. 6B. In at least some instances, shifting a location of a ring electrode towards the lead body can generate a buckling effect of the cables, so the slack can be provided to address this issue, as illustrated in FIG. 6B.

FIGS. 6C and 6D illustrate three electrode strips 142 attached to conductor 132 extending out of the lead body 106. FIGS. 6C to 6D are views looking toward the distal end of the lead body 106 and distalmost spacer 136. The electrode strips 142 are made of conductive material such as those material described above for use in electrodes.

FIG. 6E is a closeup view of an end of one of the electrode strips 142 which illustrates that each of the electrode strips includes multiple pre-electrodes 150 with each adjacent electrode pair separated by a thinner connection region 152. This alternating arrangement of pre-electrodes 150 and connection regions 152 extends along the length of each electrode strip 142. The arrangement of pre-electrodes 150 and connection regions 152 is also a longitudinal arrangement as these elements extend along the length of the electrode strip and, at least in some embodiments, the electrode strip lies parallel to the longitudinal axis of the lead and electrode carrier.

The thickness of the pre-electrodes 150 is greater than the thickness of the connection regions 152. As illustrated in FIGS. 6C to 6E, the electrode strips are curved and form an arc. Along the inner surface 154 of the electrode strips 142, the connection regions 152 are inset relative to the pre-electrodes 150 to form valleys in the inner surface. As described in more detail below, the connection regions 152 are removed by grinding or other removal method to separate the pre-electrodes 150 and form the segmented electrodes 122 (FIGS. 4A to 5G.) In at least some embodiments, as illustrated in FIG. 6E, connection regions 152 are not insert relative to the pre-electrodes 150 along the outer surface 156 so that the outer surface 156 is smooth. The electrode strips 142 can be made using any suitable method including, but not limited to, casting, molding, or the like.

Each of the pre-electrodes 150 along an electrode strip 142 corresponds to a segmented electrode in one of the sets of segmented electrodes. In the illustrated embodiment of FIG. 6C, there are ten pre-electrodes 150 on each of the electrode strips 142, so the final lead will have ten sets of segmented electrodes. Also, in the illustrated embodiment of FIG. 6C, there are three electrode strips 142 and so each set of segmented electrodes in the final lead will have three segmented electrodes, one from each electrode strip. It will be recognized, however, that other embodiments can include a different number of electrode strips including, but not limited to, two, four, five, six, or more electrode strips. Also, an electrode strip 142 may have any number of pre-electrodes 150 including, but not limited to, two, three, four, five, six, seven, eight, nine, ten, eleven, twelve, or more pre-electrodes. Each of the pre-electrodes 150 of an electrode strip will be separated from each adjacent pre-electrode by a connection region 152. In the illustrated embodiment, the electrode strips 142 are arranged so that the pre-electrodes 150 will be aligned with each other into sets of segmented electrodes in the final lead. In other embodiments, the pre-electrodes 150 of the multiple electrode strips 142 do not need to align with each other, but may form staggered arrangements such as the arrangement in FIG. 5B.

In FIGS. 6C and 6D, a conductor 132 is attached to one of the pre-electrodes 150 for illustrative purposes. However, as illustrated in FIGS. 6F and 6G, individual conductors 132 are attached to each of the pre-electrodes 150. In the illustrated embodiment, a different conductor 132 is attached to each pre-electrode 150. In other embodiments, any of the conductors 132 may be attached to multiple pre-electrodes in any desire arrangement. In at least some embodiments, each conductor 132 includes insulation 135 (FIG. 6G) around the conductor to prevent or resist conduction between conductors or between the conductor and other pre-electrodes/electrodes to which it is not attached. The insulation at the end of the conductor 132 is removed so that the conductor can be attached to the selected pre-electrode 150, as illustrated in FIGS. 6C and 6D.

The conductors 132 can be attached to the selected pre-electrodes 150 using any suitable technique including, but not limited to, welding or soldering. FIG. 6F illustrates one method of attaching a conductor 132 to a pre-electrode 150 by resistance welding using a welding electrode 158. In at least some embodiments, an adhesive may be applied to the welding site to reinforce weld strength and integrity.

One advantage of the illustrated method of making a lead is that the attachment of the conductor 132 to the pre-electrode 150 involves a process that can be directly observed. In other methods of making leads with segmented electrodes, the pre-electrode is part of a cylindrical arrangement and is often welded by applying the welding electrode to the exterior of the pre-electrode to weld a conductor to the interior of the electrode which can be less efficient process and may be more prone to failed welds.

As illustrated in FIG. 6H, after placement of the electrode strips 142 onto the lead, an electrode carrier 160 is slid onto the mandrel 131. FIG. 6I illustrates a portion of one embodiment of the electrode carrier 160 and FIG. 6J is a cross-section of the electrode carrier 160. In the illustrated embodiment, the electrode carrier 160 has a body 162 that defines a central lumen 164, a center segment 166 disposed around the central lumen, and rails 168 extending from the center segment. In at least some embodiments, the number of rails 168 equals the number of electrode strips 142.

In at least some embodiments including the illustrated embodiment, the electrode carrier 160 is advanced until the electrode carrier engages the distal-most spacer 136. In other embodiments, the electrode carrier 160 can be advanced until the electrode carrier engages the lead body 106 including advancing beneath the spacers 136 and ring electrodes 120. In yet other embodiments, the electrode carrier 160 may be inserted over the mandrel 131 prior to placement of the spacers 136 and ring electrodes 120 or placement of the electrode strips 142 over the mandrel 131 with one or more of these components being inserted over the electrode carrier. In other embodiments, the electrode carrier 160 may extend into the lead body 106 (and, optionally, along a part of the length or the entire length of the lead) with the spacers 136, ring electrodes 120, and electrode strips 142 being inserted over the electrode carrier.

As illustrated in FIG. 6K to 6M, the electrode strips 142 are then laid down on the electrode carrier 160. In at least some embodiments, a constraining ring 190 is positioned around the electrode strips 142 to temporarily hold the electrode strips in place.

The electrode carrier 160 includes a number of features to facilitate placement of the electrode strips 142. The electrode carrier 160 includes divider segments 170 as part of the rails 168 to separate the electrode strips 142 from each other and, in the final lead, to separate the segmented electrodes from each other in each set of segmented electrodes. In at least some embodiments, the number of divider segments 170 equals the number of electrode strips 142.

The electrode carrier 160 also includes shoulder segments 172 as part of the rails 168. The shoulder segments 172 are disposed between the divider segment 170 and the center segment 166. In the illustrated embodiment, the shoulder segment 172 extends circumferentially to both sides of the divider segment 170 to provide a shoulder or platform upon which an edge portion of the electrode strip 142 can lie, rest or is otherwise supported or disposed upon, as illustrated in FIGS. 6L and 6M.

In addition, conductor channels 174 are formed between the electrode carrier 160 and the electrode strips 142. Each conductor channel 174 is bounded by an electrode strip 142, the central segment 166 of the electrode carrier 160, and the shoulder segments 172 of adjacent rails 168 of the electrode carrier 160. Turning back to 6G, the conductors 132 are attached to the pre-electrodes 150 so that the conductors will lie within the conductor channels 174 (FIGS. 6L and 6M).

In the illustrated embodiment, the electrode rings 120 and spacers 136 are positioned prior to adding the electrode strips 142. Alternatively or additionally, one or more electrode rings 120 and spacers 136 can be added distal to the electrode strips 142 by positioning the electrode ring(s) 120 and spacer(s) 136 on the electrode carrier 160 after the electrode strips 142 are laid down onto the electrode carrier (in which case the electrode carrier will extend distally beyond the electrode strips.) It will also be understood, that other electrode arrangements can be formed by adding more electrode strips distal to the original electrode strips and essentially repeating the steps illustrated in FIGS. 6C to 6M for this second set of electrode strips.

In at least some embodiments, the electrode rings 120, spacers 136, and electrode strips 142 may be pulled away from the lead body 106 to straighten the conductor 132 (see, FIG. 6H). A spacer (not shown) can be positioned between the proximal-most electrode ring 120 and the lead body 106 and, optionally, reflowed to form an additional portion of the lead body 106a (FIG. 6K) covering the conductors. The spacer (which forms lead body 106a) can be made of the same or different material from the lead body 106.

As illustrated in FIGS. 6N and 6O, a sleeve 176 is disposed over the electrode strips 142 and electrode carrier 160. The sleeve 176 is open at a distal end 178. The sleeve 176 can be made of any suitable material including, but not limited to, heat shrink tubing.

Non-conductive material is injected through the open distal end 178 of the sleeve 176 to fill the conductor channels 174 and to also fill inset area associated with the connection regions 152 (FIGS. 6D and 6E) and any other suitable areas. In at least some embodiments, the area between the divider segments 170 and the sleeve 176 may be filled if, for example, the divider segments are inset relative to the outer surfaces of the electrode strips. In at least some embodiments, the non-conductive material is injected in a fluid or flowable form and then hardens using any suitable technique including, but not limited to, cooling, thermosetting, cross-linking, or the like. Examples of suitable non-conductive material include, but are not limited to, silicone, polyurethane, epoxy, or the like. The non-conductive material forms a portion 106b (FIGS. 6P, 6Q, and 6R) of the lead body.

In at least some embodiments, the injected non-conductive material may be made of a same or different material as the electrode carrier 160 or the lead body 106 or spacer that forms the lead body 106a (or any combination of these elements). In at least some embodiments, the electrode carrier 160 may be heated to make the material of the electrode carrier flow into (e.g., reflow) or adhere to the injected non-conductive material.

In at least some embodiments, the mandrel 131 remains inserted in the central lumen 164 of the electrode carrier 160 to prevent filling of the central lumen. In at least some embodiments, the non-conductive material may be used to form a lead tip 180 (FIG. 6P). In other embodiments, a lead tip 180 may be attached to the non-conductive material prior to hardening of the non-conductive material or after hardening using an adhesive or any other suitable attachment method. In yet other embodiments, the lead tip 180 may be attached using adhesive or other suitable attachment method after hardening of the non-conductive material. In at least some embodiments, the mandrel 131 is removed prior to formation or attachment of the lead tip 180. In yet other embodiments, the mandrel 131 may be removed from the other end of the lead after formation or attachment of the lead tip 180.

After the non-conductive material is hardened, the portion of the lead with the electrode strips 142 is ground down (for example, using centerless grinding) or otherwise processed to remove an outer portion of the lead and separate the segmented electrodes 122 for each other, as illustrated in FIGS. 6P, 6Q, and 6R. In at least some embodiments, the sleeve 176 may be removed before grinding. In other embodiments, the sleeve 176 may be removed as part of the grinding. By the grinding (or other removal process), the connection regions 152 (FIG. 6E) of the electrode strips 142 are removed to leave the pre-electrodes 150 (FIG. 6E) which now form segmented electrodes 122 in the electrode array of the lead 103. FIG. 6R illustrates in more detail, the segmented electrodes 122 and electrode carrier 160 with the lead body 106a transparent for illustration purposes. FIGS. 6P and 6Q do not illustrate the electrode carrier 160 for clarity of illustration.

The steps and portion of the lead illustrated in FIGS. 6A to 6R demonstrate the formation of segmented electrodes on the distal end of a lead. It will be understood that the same or similar steps can be used to form segmented terminals on the proximal end of a lead or lead extension.

Figure 7:
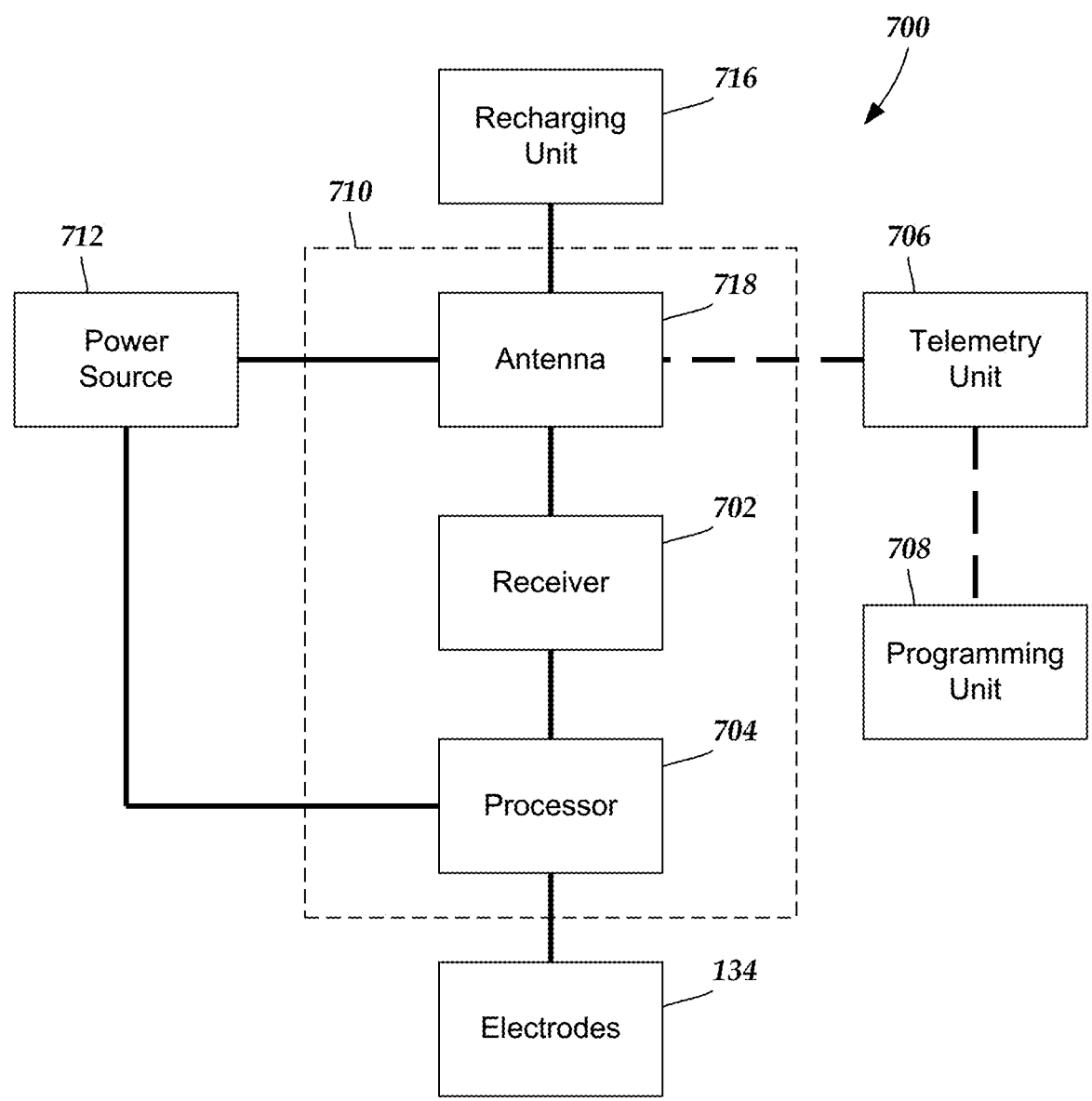
FIG. 7 is a schematic overview of one embodiment of components of an electrical stimulation system.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, amplitude, width, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:

1. An electrical stimulation lead having a proximal portion, a distal portion, and a circumference, the electrical stimulation lead comprising
   a plurality of terminals disposed along the proximal portion of the electrical stimulation lead;
   a plurality of electrodes disposed along the distal portion of the electrical stimulation lead, the plurality of electrodes comprising a plurality of segmented electrodes, wherein each segmented electrode extends around no more than 75% of the circumference of the electrical stimulation lead;
   a plurality of conductors electrically coupling the terminals to the electrodes; and
   an electrode carrier, wherein the electrode carrier comprises a center segment, a plurality of shoulder segments extending from the center segment, and a plurality of divider segments, each of the divider segments extending from one of the shoulder segments, wherein each of the divider segments is disposed between, and separates, at least two of the segmented electrodes, wherein a plurality of the segmented electrodes are each disposed on a shoulder of at least one of the shoulder segments.

2. The electrical stimulation lead of claim 1, wherein the electrode carrier and the segmented electrodes, in combination, define a plurality of conductor channels bounded by the electrode carrier and the segmented electrodes, wherein each of the conductor channels comprises a portion of at least one of the conductors.

3. The electrical stimulation lead of claim 1, wherein each of the shoulder segments forms two shoulders on opposite sides of the divider segment extending from the shoulder segment.

4. The electrical stimulation lead of claim 1, wherein the plurality of the segmented electrodes are each disposed on the shoulder of at least two of the shoulder segments.

5. The electrical stimulation lead of claim 1, further comprising a lead body disposed over at least part of the electrode carrier.

6. The electrical stimulation lead of claim 1, wherein the electrode carrier defines a central lumen.

7. A system for electrical stimulation, the system comprising:
the electrical stimulation lead of claim 1; and
a control module electrically coupleable to the electrical stimulation lead.

8. An electrical stimulation lead having a proximal portion, a distal portion, and a circumference, the electrical stimulation lead comprising
a plurality of terminals disposed along the proximal portion of the electrical stimulation lead;
a plurality of electrodes disposed along the distal portion of the electrical stimulation lead, the plurality of electrodes comprising a plurality of segmented electrodes, wherein each segmented electrode extends around no more than 225% of the circumference of the electrical stimulation lead;
a plurality of conductors electrically coupling the terminals to the electrodes; and
an electrode carrier, wherein the electrode carrier comprises a center segment and a plurality of rails, each of the rails extending from the center segment, wherein a portion of each of the rails is disposed between, and separates, at least two of the segmented electrodes, wherein the electrode carrier and the segmented electrodes, in combination, define a plurality of conductor channels bounded by the electrode carrier and the segmented electrodes, wherein each of the conductor channels comprises a portion of at least one of the conductors.

9. The electrical stimulation lead of claim 8, wherein each of the segmented electrodes is disposed on a portion of at least one of the rails of the electrode carrier.

10. The electrical stimulation lead of claim 8, wherein each of the rails comprises a shoulder segment and a divider segment disposed on the shoulder segment, wherein each of the shoulder segments forms two shoulders on opposite sides of the divider segment of the rail.

11. The electrical stimulation lead of claim 10, wherein the plurality of the segmented electrodes are each disposed on the shoulder of at least two of the shoulder segments.

12. The electrical stimulation lead of claim 8, further comprising a lead body disposed over at least part of the electrode carrier.

13. The electrical stimulation lead of claim 8, wherein the electrode carrier defines a central lumen.

* * * * *